United States Patent
Smith et al.

(10) Patent No.: US 11,419,864 B2
(45) Date of Patent: Aug. 23, 2022

(54) MARKERS OF TISSUE AGING AND USES THEREFOR

(71) Applicant: The University of Newcastle, Newcastle (AU)

(72) Inventors: Roger Smith, Newcastle (AU); Kaushik Maiti, Charlestown (AU)

(73) Assignee: The University of Newcastle, Newcastle (AU)

( * ) Notice: Subject to any disclaimer, the term of this patent is extended or adjusted under 35 U.S.C. 154(b) by 0 days.

(21) Appl. No.: 16/490,287

(22) PCT Filed: Mar. 2, 2018

(86) PCT No.: PCT/AU2018/050190
§ 371 (c)(1),
(2) Date: Aug. 30, 2019

(87) PCT Pub. No.: WO2018/157213
PCT Pub. Date: Sep. 7, 2018

(65) Prior Publication Data
US 2020/0306241 A1   Oct. 1, 2020

(30) Foreign Application Priority Data

Mar. 3, 2017 (AU) ................................ 2017900740

(51) Int. Cl.
| | | |
|---|---|---|
| *A61K 31/473* | (2006.01) | |
| *A61P 15/00* | (2006.01) | |
| *A61K 31/4436* | (2006.01) | |
| *A61K 31/4535* | (2006.01) | |
| *C12Q 1/26* | (2006.01) | |
| *C12Q 1/6883* | (2018.01) | |

(52) U.S. Cl.
CPC ........ *A61K 31/473* (2013.01); *A61K 31/4436* (2013.01); *A61K 31/4535* (2013.01); *A61P 15/00* (2018.01); *C12Q 1/26* (2013.01); *C12Q 1/6883* (2013.01); *C12Q 2600/156* (2013.01); *C12Q 2600/158* (2013.01)

(58) Field of Classification Search
CPC .............................. A61K 31/473; A61P 15/00
See application file for complete search history.

(56) References Cited

U.S. PATENT DOCUMENTS 5,393,763 A   2/1995 Black et al.

OTHER PUBLICATIONS

Wong et al., "Raloxifene protects endothelial cell function against oxidative stress", British Journal of Pharmacology, vol. 155, No. 3, pp. 326-334 (2008).*
Maiti, et al., The Human Placenta at 41 Weeks of Gestation shows Evidence of Aging with Shortened Telomeres, DNA Oxidation and Changes in IGFR2, Autophagy and MTOR, P2.38., Abstracts/Placenta 36 (2015) A49.
Osmanova, et al., The effects of raloxifene treatment on oxidative status in brain tissues and learning process of ovariectomized rats, Iranian Journal of Reproductive Medicine, vol. 9, No. 4, pp. 295-300, Autumn 2011.
Maiti, et al.. Evidence that fetal death is associated with placental aging, American Journal of Obstetrics & Gynecology, pp. 441.e1-441.e14, Oct. 2017, Elsevier Inc.
Shaker, et al., Pathogenesis of preeclampsia: Implications of apoptotic markers and oxidative stress, Human and Experimental Toxicology, 32(11), 1170-1178, 2013, The Author(s).
Khatri, Meena, Circulating biomarkers of oxidative stress in normal pregnancy and preeclampsia and efficacy of antioxidant supplementation, International Journal of Reproduction, Contraception, Obstetrics and Gynecology, vol. 2, Issue 3, Sep. 2013, pp. 304-310.
Gil, et al., Malondialdehyde: A Possible Marker of Ageing, Gerontology, Jul./Aug. 2002; 48, 4 pp. 209-214, S. Karger AG.
Min, et al.. Effect of Oxidative Stress on Birth Sizes: Consideration of Window from Mid Pregnancy to Delivery, Placenta, 30, 2009, pp. 418-423, Elsevier Ltd.
Vanderlelie, et al., Increased Biological Oxidation and Reduced Anti-oxidant Enzyme Activity in Pre-eclamptic Placentae, Placenta vol. 26, 2005, pp. 53-58, Elsevier Ltd.
Smith, et al., Unexplained antepartum stillbirth: A consequence of placental aging?, Placenta, 34, 2013 pp. 310-313, Elsevier Ltd.
Londero, et al., Placental aging and oxidation damage in a tissue micro-array model: an immunohistochemistry study, Histochem Cell Biol, 146, 2016, pp. 191-204, Springer-Veriag Berlin Heidelberg.

* cited by examiner

*Primary Examiner* — Kevin E Weddington
(74) *Attorney, Agent, or Firm* — Howard & Howard Attorneys LLC

(57) ABSTRACT

Provided herein are methods of detecting or determining aging and/or oxidative damage in tissue, including placental tissue, skin, kidney and brain tissue. One embodiment provides a method for detecting or determining aging in body tissue, comprising measuring one or more markers of aldehyde oxidase 1 (AOX1) expression or activity in a biological sample, wherein the level of AOX1 expression or activity, or of the one or more markers, is indicative of aging in the tissue. Also provided herein are methods of treating a disease or condition associated with ageing or oxidative damage in one or more cells or tissues, comprising administering to a subject in need thereof an inhibitor of AOX1.

12 Claims, 14 Drawing Sheets

Specification includes a Sequence Listing.

A

B

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
cgtcctgtgc accttcatgt                                                      20

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
agctcatcca ggtgaggaag aa                                                   22

<210> SEQ ID NO 3
<211> LENGTH: 4949
<212> TYPE: DNA
<213> ORGANISM: Homo sapiens

<400> SEQUENCE: 3
cgccccactc ggcgggtcgg tgccgccggg tcccaggtgc ccgctacttc ccagaacctc          60
cgcctcccgc tccgggccct cgaaccagcg cggacaccac aatggaccgg gcgtccgagc         120
tgctcttcta cgtgaacggc cgcaaggtga tagaaaaaaa tgtcgatcct gaaacaatgc         180
tgttgcctta tttgaggaag aagcttcgac tcacaggaac taagtatggc tgtggaggag         240
gaggctgtgg tgcttgtaca gtgatgatat cacgatacaa ccccatcacc aagaggataa         300
ggcatcaccc agccaatgcc tgtctgattc ccatctgttc tctgtatggt gctgccgtca         360
ccacagtaga aggcatagga agcacccaca ccagaattca tcctgttcag gagaggattg         420
ccaagtgtca tggcacccag tgtggcttct gcacacctgg gatggtgatg tccatctaca         480
cgctgctcag gaaccaccca gagcccactc tggatcagtt aactgatgcc cttggtggta         540
acctgtgccg ttgcactgga tacaggccca taattgatgc atgcaagact ttctgtaaaa         600
cttcgggctg ctgtcaaagt aaagaaaatg gggtttgctg tttggatcaa ggaatcaatg         660
gattgccaga atttgaggaa ggaagtaaga caagtccaaa actcttcgca gaagaggagt         720
ttctgccatt ggatccaacc caggaactga tatttcctcc tgagctaatg ataatggctg         780
agaaacagtc gcaaaggacc agggtgtttg gcagtgagag aatgatgtgg ttttccccg         840 tgaccctgaa ggaactgctg gaatttaaat tcaagtatcc ccaggctcct gttatcatgg         900
```

```
gaaacacctc tgtgggggcct gaagtgaaat ttaaaggcgt cttttcaccca gttataattt      960 ctcctgatag aattgaagaa ctgagtgttg taaaccatgc atataatgga ctcacccttg     1020
gtgctggtct cagcctagcc caggtgaagg acattttggc tgatgtagtc cagaagcttc     1080
cagaggagaa gacacagatg taccatgctc tcctgaagca tttgggaact ctggctgggt     1140
cccagatcag gaacatggct tctttagggg gacacatcat tagcaggcat ccagattcag     1200
atctgaatcc catcctggct gtgggtaact gtaccctcaa cttgctatca aagaaggaa      1260 aacgacagat tcctttaaat gagcaattcc tcagcaagtg ccctaatgca gatcttaagc     1320
ctcaagaaat cttggtctca gtgaacatcc cctactcaag gaagtgggaa tttgtgtcag     1380
ccttccgaca agcccagcga caggagaatg cgctagcgat agtcaattca ggaatgagag     1440
tcttttttgg agaaggggat ggcattatta gagagttatg catctcatat ggaggcgttg     1500
gtccagccac catctgtgcc aagaattcct gccagaaact cattggaagg cactggaacg     1560
aacagatgct ggatatagcc tgcaggctta ttctgaatga agtctccctt ttgggctcgg     1620
cgccaggtgg gaaagtggag ttcaagagga ctctcatcat cagcttcctc ttcaagttct     1680
acctggaagt gtcacagatt tgaaaaaga tggatccagt tcactatcct agccttgcag     1740
acaagtatga aagtgcttta gaagatcttc attccaaaca tcactgcagt acattaaagt     1800
accagaatat aggcccaaag cagcatcctg aagacccaat tggccacccc atcatgcatc     1860
tgtctggtgt gaagcatgcc acgggggagg ccatctactg tgatgacatg cctctggtgg     1920
accaggaact tttcttgact tttgtgacta gttcaagagc tcatgctaag attgtgtcta     1980
ttgatctgtc agaagctctc agcatgcccg tgtggtgga catcatgaca gcagaacatc      2040
ttagtgacgt caactccttc tgcttttttta ctgaagctga gaaatttctg gcgacagata     2100
aggtgttctg tgtgggtcag cttgtctgtg ctgtgcttgc cgattctgag gttcaggcaa     2160
agcgagctgc taagcgagtg aagattgtct atcaagactt ggagccgctg atactaacaa     2220
ttgaggaaag tatacaacac aactcctcct tcaagccaga aaggaaactg gaatatggaa     2280
atgttgacga agcatttaaa gtggttgatc aaattcttga aggtgaaata catatgggag     2340
gtcaagaaca ttttttatatg gaaacccaaa gcatgcttgt cgttcccaag ggagaggatc     2400
aagaaatgga tgtctacgtg tccacacagt ttcccaaata tatacaggac attgttgcct     2460
caaccttgaa gctcccagct aacaaggtca tgtgccatgt aaggcgtgtt ggtggagcgt     2520
ttggagggaa ggtgttaaaa accggaatca ttgcagccgt cactgcattt gccgcaaaca     2580
aacatggccg tgcagttcgc tgtgttctgg aacgaggaga agacatgtta ataactggag     2640
gccgccatcc ttaccttgga aagtacaaag ctggattcat gaacgatggc agaatcttgg     2700
ccctggacat ggagcattac agcaatgcag gcgcctcctt ggatgaatca ttattcgtga     2760
tagaaatggg acttctgaaa atggacaatg cttacaagtt tcccaatctc cgctgccggg     2820
gttgggcatg cagaaccaac cttccatcca acacagcttt tcgtgggttt ggctttcctc     2880
aggcagcgct gatcaccgaa tcttgtatca cggaagttgc agccaaatgt ggactatccc     2940
ctgagaaggt gcgaatcata aacatgtaca aggaaattga tcaaacaccc tacaaacaag     3000
agatcaatgc caagaaccta atccagtgtt ggagagaatg tatggccatg tcttcctact     3060
ccttgaggaa agttgctgtg gaaaagttca atgcagagaa ttattggaag aagaaaggac     3120
tggccatggt cccccctgaag tttcctgttg gccttggctc acgtgctgct ggtcaggctg     3180
ctgccttggt tcacatttat cttgatggct ctgtgctggt cactcacggt ggaattgaaa     3240
```

-continued

```
tggggcaggg ggtccacact aaaatgattc aggtggtcag ccgtgaatta agaatgccaa    3300
tgtcgaatgt ccacctgcgt ggaacaagca cagaaactgt ccctaatgca aatatctctg    3360
gaggttctgt ggtggcagat ctcaacggtt tggcagtaaa ggatgcctgt caaactcttc    3420
taaaacgcct cgaacccatc atcagcaaga atcctaaagg aacttggaaa gactgggcac    3480
agactgcttt tgatgaaagc attaaccttt cagctgttgg atacttcaga ggttatgagt    3540
cagacatgaa ctgggagaaa ggcgaaggcc agcccttcga atactttgtt tatggagctg    3600
cctgttccga ggttgaaata gactgcctga cgggggatca taagaacatc agaacagaca    3660
ttgtcatgga tgttggctgc agtataaatc cagccattga cataggccag attgaaggtg    3720
catttattca aggcatggga ctttatacaa tagaggaact gaattattct ccccagggca    3780
ttctgcacac tcgtggtcca gaccaatata aaatccctgc catctgtgac atgcccacgg    3840
agttgcacat tgctttgttg cctccttctc aaaactcaaa tactctttat tcatctaagg    3900
gtctgggaga gtcgggggtg ttcctggggt gttccgtgtt tttcgctatc catgacgcag    3960
tgagtgcagc acgacaggag agaggcctgc atggaccctt gacccttaat agtccactga    4020
ccccggagaa gattaggatg gcctgtgaag acaagttcac aaaaatgatt ccgagagatg    4080
aacctggatc ctacgttcct tggaatgtac ccatctgaat caaatgcaaa cttctggaga    4140
aaacagagtg cctcttccca gatggcaatc tgtcctatct ctgtgctgga agatgctaga    4200
tctgaaagac agagtttcca cagttcagaa atcatcccac agtgttgctt ttctatggag    4260
ctgatttaaa gtattccatt tagatttgat agatatgctt aagcaatcta taaatcattt    4320
tcaatgttat aaacactaat tggtttcctc tagggtgata ttcgtcatta ctctgtctct    4380
tcaatccatc cagctaaatg gaataggtga tgacttgcat gtgactccta cttggcttct    4440
atccaccaac agaaattata ccatatagtg aaaggcaatt ttctaaataa tttcattact    4500
aatatgaact gtgaagttgt cattttttca tttgtccttt tctgctatca ccttcctctt    4560
gtcagaatga atatagacac tgtatctaag tgggaccaaa gaaaaaatag cgaactttca    4620
ccaaagtttt catgaaaacc caaaagcttt aaaagttact atcaagaaat tgaaaggaaa    4680
cccacagaat aggataaaat atttgtaaat catatatttg ataaaagtct tgtaaccaga    4740
tacataaaga gctcttacaa ctcaataaaa ggcaagtaat ttaaaaatag gcaaaagaat    4800
tgctggatgg tatggtagtt ctattttttag tttttacccct aactactctg acttgatcat    4860
ttaacattct gtgtatgtaa caaaatatca catgcataaa tattatgtat caataaaatt    4920
ttttaatggg caaaaaaaaa aaaaaaaa                                       4949
```

MARKERS OF TISSUE AGING AND USES THEREFOR

CROSS-REFERENCE TO RELATED APPLICATION(S)

The present application is a U.S. National Stage of International Patent Application No. PCT/AU2018/050190, filed on Mar. 2, 2018, and which claims priority to Australian Patent Application No. 2017900740, filed Mar. 3, 2017, both disclosures of which are hereby incorporated by reference in their entirety for all purposes.

FIELD OF THE ART

The present disclosure relates generally to methods of detecting or determining aging and/or oxidative damage in tissue, such as placental tissue, skin, kidney and brain tissue. The disclosure also relates to methods of delaying, slowing or preventing aging and/or oxidative damage in such tissue.

SEQUENCE LISTING

This disclosure, in accordance with 37 CFR § 1.52, incorporates by reference the sequence listing material contained within text file titled "068612.00009_ST25.txt", created on Jan. 2, 2020 and totaling 7,124 bytes.

BACKGROUND

Accumulated random damage to tissue may affect tissue functionality and contribute to aging. Metabolic processes and growth of cells generate reactive oxygen species that may cause damage to proteins, lipids and nucleic acids. While cells possess defence mechanisms against oxidative stress, such as enzymes like catalase and superoxide dismutase, if the repair mechanisms are inadequate to compensate for the generation of reactive oxygen species, damage and aging of the tissue may occur.

Growth pathways are generally associated with increased oxidative stress. Due to the placenta's function in promoting the growth of a fetus it is not surprising that indicators of oxidative damage can be found in the placenta, in particular nearing the end of pregnancy when fetal growth is rapid. The inventors have hypothesised that stillbirth may be related to a reduced ability of the ageing placenta to sustain the fetus (Smith et al 2013, *Placenta*, 34:310-313). Supporting this view a histopathological study of placentas associated with cases of unexplained intrauterine death at term revealed that 91% showed thickening of the maternal spiral artery walls, 54% contained placental infarcts, 10% had calcified areas and 13% demonstrated vascular occlusion; changes that are associated with aging in other organs. The inventors demonstrated that placentas from women who delivered late or had stillbirth had biochemical evidence of aging and oxidative stress.

Unexplained fetal death is a common complication of pregnancy occurring in approximately 1 in 200 pregnancies in developed countries and more frequently in the developing world. Unexplained fetal death is 40 times more common than sudden infant death syndrome but attracts far less attention, yet for the families involved the event is devastating. While no cause has been established, stillbirth may be associated with fetal growth restriction, congenital abnormality, antepartum haemorrhage, perinatal infection, preeclampsia and maternal factors such as maternal height and age, obesity, hypertension, diabetes, smoking, parental consanguinity, ethnicity and country of birth. While there are risk factors for stillbirth, the cause of many cases remains unexplained.

In some antepartum cases, lack of movement of the fetus may occur prior to stillbirth, although there may be no warning signs. The lack of understanding of the cause of stillbirth makes prediction of risk during pregnancy difficult. Stillbirth can be defined as death of a fetus before or during birth at more than or equal to 20 weeks gestation or of more than or equal to 400 g birthweight (Perinatal Society of Australia and New Zealand Clinical Practice Guideline for Perinatal Mortality; Second Edition, version 2.2, April 2009). Identifying indicators of risk of stillbirth may provide an opportunity for pregnant women to undergo prophylactic caesarean section or induction of labour to reduce risk to the fetus. Therefore prognostic biomarkers for stillbirth risk would be highly beneficial in prevention of stillbirth.

The optimal length of a pregnancy is likely to differ between individuals. While a baby may be viable if born preterm, complications are likely if adequate development has not occurred in utero. In general a longer gestation (up to approximately 41 weeks) is associated with better development of a baby's anatomy and physiological systems. Indeed, infants born at 41 weeks gestation are less likely to require special education later in life than infants born at 37 weeks gestation. However, a prolonged gestational period can result in post-maturity symptoms, where the fetus continues to grow and to require additional supplies of nutrients. Post-maturity syndrome is a condition seen in post-dated infants who show evidence of late gestation failure of nutrition. Normal human infants born at term have 12-14% body fat whereas post maturity syndrome is associated with the birth of a baby with severe wrinkling of the skin due to loss of subcutaneous fat. Post maturity syndrome is rarely seen in modern obstetric practice where delivery is usually affected before 42 weeks of gestation using induction of labour or caesarean section if labour has not occurred spontaneously. Notably, the risk of stillbirth is significantly increased in post-term pregnancies, the rate rising exponentially as gestation progresses beyond 38 weeks. Therefore there appears to be a window of optimal gestation in pregnancy, however this window is likely to differ between individuals. There is currently no way to determine the ideal gestational window for individual pregnancies. While placental ageing may be an indicator of an appropriate time to deliver a baby, there is currently no method to determine the oxidative state of the placenta in a pregnant woman with minimal risk to the fetus.

SUMMARY OF THE DISCLOSURE

The present disclosure is predicated on the inventors' surprising discovery that aldehyde oxidase 1 (AOX1) expression and activity (and levels of markers thereof such as 4-hydroxynonenal, 4HNE) correlates with tissue aging and oxidative damage in multiple tissue including placenta and kidney. The inventors have also demonstrated that oxidative stress in the placenta may be reduced by the administration of inhibitors of AOX1 such as raloxifene, or G-protein-coupled estrogen receptor 1 (GPER1) agonists, such as G1. As exemplified herein inhibition of AOX1 prevents oxidative and lysosomal changes in placental tissue. The inventors therefore have identified an effective biomarker that may be non-invasively sampled to give an indication of placental oxidative stress, thereby indicating that a pregnancy may be at risk of stillbirth. Oxidative and lysosomal changes similar to those observed in the placenta can also be found in diseases associated with ageing (e.g. Alzheimer's disease, Huntington's disease). Accordingly, AOX1 also provides a marker of, and a target for treatment or prevention of, oxidative damage and ageing in multiple tissue types.

A first aspect of the present disclosure provides a method for detecting or determining aging in body tissue, the method comprising measuring one or more markers of aldehyde oxidase 1 (AOX1) expression or activity in a biological sample obtained from a subject, wherein the level of AOX1 expression or activity, as determined by the level(s) of the one or more markers, is indicative of aging in the tissue.

In an embodiment, the tissue is selected from placental tissue, skin, kidney or brain tissue.

In an exemplary embodiment, the subject is pregnant and the tissue is placental tissue.

The biological sample may be, for example, a sample of the relevant tissue, or a fluid sample, such as blood (whole blood, plasma or serum), urine, saliva or amniotic fluid. In embodiments in which the subject is pregnant, the sample may comprise, for example, maternal blood, fetal blood, urine, saliva or amniotic fluid. In embodiments in which the subject is pregnant, the biological sample is typically of maternal origin, optionally maternal blood. In other embodiments in which the subject is pregnant, the biological sample may comprise a derivative of a sample from the pregnant subject, placental tissue and/or a fetus, such as total RNA derived from maternal blood, where the total RNA may be maternal, placental or fetal in origin.

The one or more markers of AOX1 expression or activity may be measured from material released from aging tissue into the blood. In an embodiment in which the subject is pregnant, the one or more markers of AOX1 expression or activity may be measured from material released from aging placental tissue into the maternal blood. The one or more markers may therefore be measured in maternal blood. In exemplary embodiments, the one or more markers are derived from free RNA or DNA, fragments of placental cells, exosomes or microparticles present within the biological sample.

Expression of AOX1 may be measured at the mRNA or gene level, or at the polypeptide or protein level. In exemplary embodiments, a suitable marker of AOX1 expression or activity may comprise AOX1 mRNA. In other embodiments, a suitable marker of AOX1 expression or activity may comprise a molecule downstream of AOX1, such as a lipid peroxidation product. Exemplary lipid peroxidation products are 4-hydroxynonenal (4HNE) and malondialdehyde (MDA). Other products of oxidative damage that may be measured include 8-hydroxy-deoxyguanosine (8OHdG), 8-hydroxyguanosine (8HOG). In exemplary embodiments, any two or more markers of AOX1 expression or activity may be determined or measured in combination. For example, AOX1 mRNA may be measured in combination with a lipid peroxidation product such as 4HNE.

Typically, the level of expression or activity of AOX1 in a subject, as determined by the one or more markers, is compared to a reference value or values of AOX1 expression or activity, or one or more markers thereof, in tissue in which oxidative damage is not present. A reference value may be obtained or derived from one or more control or reference individuals. Alternatively, a reference value may be derived from one or more biological samples obtained from the subject at different time points which may be used as a baseline value to which a further biological sample from the subject may be compared. A person skilled in the art would be familiar with ways of determining and selecting an appropriate reference sample.

Typically an increased level of expression or activity of AOX1, or one or more markers thereof, in a biological sample from a subject compared to a reference value is indicative of oxidative stress and/or aging in the tissue. In exemplary embodiments, the tissue is placental tissue and the biological sample is maternal blood.

In particular embodiments, additional markers of oxidative stress, such as placental or fetal oxidative stress, may also be measured in the biological sample, or in a further biological sample. Non-limiting examples of such additional oxidative damage or stress markers may include AOX1 protein, glutathione, or protein carbonyls.

In embodiments in which the subject is pregnant, the method may be carried out one or more times at any time during pregnancy, in particular in the latter half of the pregnancy, such as from approximately 20 weeks gestation in the case of a human subject. In particular embodiments the method may be carried out in a post-dated pregnancy, for example after 40 weeks gestation in the case of a human subject.

A specific application of a method of the present disclosure is to detect aging in the placenta of a pregnant subject in order to predict the risk of stillbirth, wherein an increased level of expression or activity of AOX1, or one or more markers thereof, in a biological sample compared to a reference value(s) is indicative of placental aging and the risk of stillbirth. Aging of the placenta may be associated with placental and/or fetal oxidative damage, reduced fetal health and increased risk of stillbirth. Placental oxidative stress and placental aging may also be associated with inadequate nutrient transfer to a fetus. The method may also be used to diagnose pre-eclampsia in a pregnant subject or to diagnose intra-uterine growth restriction in a fetus. The method may also be used to predict the risk of, or associated with, a post-dated pregnancy.

A further embodiment of the present disclosure comprises obtaining a biological sample from a pregnant subject and measuring one or more markers of placental AOX1 expression or activity in the biological sample in order to determine the need for intervention to prevent stillbirth in a pregnancy, wherein increased AOX1 expression or activity, or levels of one or more markers thereof, compared to a reference value(s) indicates intervention may be required. Such interventions may include prophylactic caesarean section, induction of labour and/or administration of a therapy to prevent or delay placenta ageing or prolong viability of the fetus in utero. Therefore, in an embodiment, the method may be used to determine an appropriate time to deliver a baby, by determining whether placental oxidative stress is at a level where the fetus is at risk of stillbirth. Increased AOX1 expression or activity, or levels of one or more markers thereof, compared to a reference value(s) may be suggestive or indicative of an appropriate time to deliver a baby.

In an embodiment, a method of the disclosure may be used to monitor the risk of stillbirth during a pregnancy by detecting or determining aging in placental tissue by measuring one or more markers of AOX1 expression or activity in one or more biological samples obtained from a subject over time. In such a method, biological samples are obtained from a pregnant subject at multiple time points during the pregnancy, for example on a fortnightly, weekly or daily basis, and one or more markers of placental AOX1 expression or activity are measured in each biological sample from each time point. An increase in AOX1 expression or activity, or levels of one or more markers thereof, over time may be indicative of increased risk of stillbirth, and thus may be indicative of the need for intervention to prevent stillbirth.

A second aspect of the present disclosure provides a method for detecting placental aging, the method comprising obtaining a biological sample from a pregnant subject and measuring one or more markers of placental AOX1 expression or activity in the biological sample, wherein the level of AOX1 expression or activity or of the one or more markers thereof is indicative of placental aging.

Typically increased AOX1 expression or activity, or levels of one or more markers thereof, compared to a reference value(s) indicates aging in the placenta. A suitable reference value may be derived or obtained from a sample from tissue of one or more individuals in which placental tissue does not exhibit signs of oxidative damage, or may be derived or obtained from the subject at an earlier time point during the pregnancy.

The placental aging may be associated with increased risk of stillbirth, with pre-eclampsia, with intra-uterine growth restriction in the fetus, and/or with an increased risk of a post-dated pregnancy.

A third aspect of the present disclosure provides a method for predicting the risk of stillbirth in a pregnancy, the method comprising obtaining a biological sample from a pregnant subject and measuring one or more markers of placental AOX1 expression or activity in the biological sample, wherein the level of AOX1 expression or activity, or of the one or more markers thereof, is indicative of risk of stillbirth.

The risk of stillbirth may be determined directly or indirectly. For example the level of AOX1 expression or activity, or of the one or more markers thereof, may be indicative of pre-eclampsia, with intra-uterine growth restriction in the fetus, and/or with an increased risk of post-dated pregnancy, each of these being indicators or factors associated with an increased risk of stillbirth.

Typically increased AOX1 expression or activity, or levels of one or more markers thereof, compared to a reference value(s) is indicative of stillbirth risk. A reference value may be obtained or derived from one or more control or reference individuals. A suitable reference value may be derived or obtained from a sample from tissue of one or more individuals in which placental tissue do not exhibit signs of oxidative damage, or may be derived or obtained from the subject at an earlier time point during the pregnancy.

Accordingly, a fourth aspect of the present disclosure provides a method for determining the need for intervention to prevent post-dated pregnancy or stillbirth in a pregnancy, the method comprising obtaining a biological sample from a pregnant subject and measuring one or more markers of placental aldehyde oxidase 1 (AOX1) expression or activity in the biological sample, wherein the level of AOX1 expression or activity, or of the one or more markers thereof, is indicative of the need for intervention.

Intervention may comprise at least one of prophylactic caesarean section, induction of labour or administration of a therapy to delay placenta aging or prolong viability of the fetus in utero. Where the fetus is too premature to deliver safely or is too underdeveloped to be viable, an intervention may comprise treatment of the subject to reduce oxidative stress or AOX1 expression or activity as discussed in further aspects and embodiments of the present disclosure.

A fifth aspect of the present disclosure provides a method for detecting placental oxidative stress, the method comprising obtaining a biological sample from a pregnant subject and measuring one or more markers of placental AOX1 expression or activity in the biological sample, wherein the level of AOX1 expression or activity, or of the one or more markers thereof, is indicative of placental oxidative stress.

Typically increased AOX1 expression or activity, or levels of one or more markers thereof, compared to a reference value(s) is indicative of placental oxidative stress. A reference value may be obtained or derived from one or more control or reference individuals. A suitable reference value may be derived or obtained from a sample from tissue of one or more individuals in which placental tissue do not exhibit signs of oxidative damage, or may be derived or obtained from the subject at an earlier time point during the pregnancy.

A sixth aspect of the present disclosure provides a method for monitoring placental aging, placental oxidative stress or the risk of post-dated pregnancy or stillbirth over the course of a pregnancy, the method comprising: (i) obtaining a biological sample from a pregnant subject at a first time point during the course of a pregnancy; (ii) measuring one or more markers of placental AOX1 expression or activity in the biological sample; (iii) obtaining one or more further biological samples from the subject at one or more later time points during the pregnancy; and (iv) measuring one or more markers of placental AOX1 expression or activity in the one or more further biological samples, wherein an increase in the level of AOX1 expression or activity, or of the one or more markers thereof, over time is indicative of placental aging, placental oxidative stress or the risk of post-dated pregnancy or stillbirth.

Measurement of the one or more markers may begin, for example, in mid gestation. In an exemplary embodiment biological samples may be obtained from about 20 weeks gestation. Intervals between the time points may be determined by a person skilled in the art and may be daily, weekly, fortnightly, monthly, or another appropriate time period determined by a practitioner. The time points may increase in frequency throughout the course of pregnancy, particularly at later gestational ages.

In a seventh aspect of the present disclosure there is provided a method of slowing or preventing aging or oxidative damage in one or more cells or tissues, the method comprising exposing the one or more cells or tissues to an inhibitor of AOX1.

The inhibitor may act directly or indirectly on AOX1. In an exemplary embodiment, the inhibitor of AOX1 is raloxifene or a G protein-coupled estrogen receptor 1 (GPER1) agonist. An exemplary GPER1 agonist is G-1 ((1-[4-(6-bromobenzo[1,3] dioxol-5yl)-3a,4,5,9b-tetrahydro-3H-cyclopenta[c]quinolin-8-yl]-ethanone).

In an exemplary embodiment the tissue is placental tissue. Accordingly, the inhibitor of AOX1 is administered to a pregnant subject.

In a further exemplary embodiment, the tissue is skin, kidney or brain tissue.

In an eighth aspect of the present disclosure there is provided a method of treating a disease or condition associated with aging or oxidative damage in one or more cells or tissues, the method comprising administering to a subject in need thereof an inhibitor of AOX1.

In a ninth aspect of the present disclosure there is provided a method for preventing or reducing the risk of post-dated pregnancy or stillbirth, the method comprising administering to a pregnant subject an inhibitor of AOX1.

Further aspects provide the use of an inhibitor or AOX1 in the manufacture of a medicament for lowing or preventing aging or oxidative damage, for treating a disease or condition associated with aging or oxidative damage, or for preventing or reducing the risk of post-dated pregnancy or stillbirth.

BRIEF DESCRIPTION OF THE DRAWINGS

Aspects and embodiments of the present disclosure are described herein, by way of non-limiting example only, with reference to the following drawings.

In FIGS. 5D to 5G each coloured line represents results on an individual placenta, and shows the mean intensity of LAMP2 across the syncytiotrophoblast at 5 random sites per image (example represented by light green line in 5A, 5B and 5C) for 6 separate images per placenta. Images were photographed at 100× magnification and 1.4 optical resolution. Scale bar, 20 µm.

DETAILED DESCRIPTION

Figure 1:
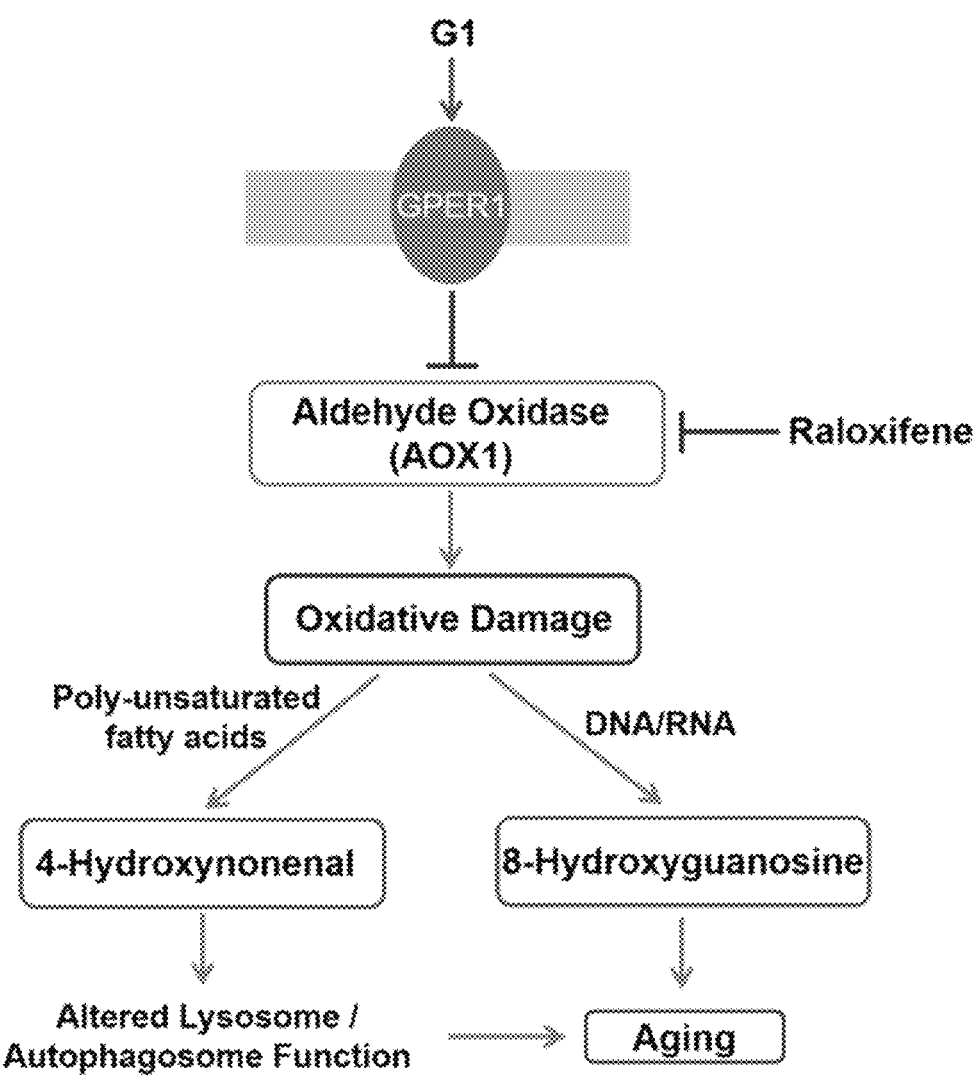
FIG. 1: Aldehyde oxidase regulates oxidative damage in placentas associated with stillbirth. Oxidative damage to fatty acids can be demonstrated by 4-hydroxynoneal (4HNE), which is associated with altered lysosome and/or autophagosome function. Oxidative damage can also alter nucleic acids (DNA and/or RNA) in the cell, which may be demonstrated by the presence of 8-hydroxy-guanosine (8OHdG) or 8-hydroxyguanosine (8HOG). 4HNE, 8OHdG and 8HOG can be indicative of ageing in the placenta. Aldehyde oxidase may be inhibited by raloxifene and by using the agonist G1 to interact with the G protein-coupled estrogen receptor 1.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, typical methods and materials are described.

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

As used herein, the term "subject" includes any mammal, such as humans, non-human primates, livestock animals (eg. sheep, pigs, cattle, horses, donkeys, goats), laboratory test animals (eg. mice, rabbits, rats, guinea pigs, other rodents), and companion animals (eg. dogs, cats). In a typical embodiment, the subject is a human. Similarly, the term "individual" includes any mammal, such as humans, non-human primates, livestock animals (eg. sheep, pigs, cattle, horses, donkeys, goats), laboratory test animals (eg. mice, rabbits, rats, guinea pigs, other rodents), and companion animals (eg. dogs, cats). In a typical embodiment, the individual is a human.

The term "stillbirth" herein refers to death of a fetus before or during birth at more than or equal to about 20 weeks gestation or of more than or equal to about 400 g birthweight (Perinatal Society of Australia and New Zealand Clinical Practice Guideline for Perinatal Mortality; Second Edition, version 2.2, April 2009).

The term "post-dated" refers to pregnancies beyond the expected gestation time. In the context of this disclosure, when referring to human pregnancy, the term "post-dated" is used to indicate a pregnancy greater than 40 completed weeks of gestation. A post-dated pregnancy may also be referred to as a post-term pregnancy.

The term "oxidative stress", as used herein, may be used interchangeably with the term "oxidative damage" and refers to an imbalance between reactive oxygen species and antioxidant mechanisms and damage caused by such imbalance. Non-limiting examples of oxidative damage include the oxidation of nucleic acids, such as DNA or RNA, which may be detected in a sample by, for example, analysis or measurement of 8-hydroxy-deoxyguanosine or 8-hydroxyguanosine (8OHdG or 8HOG), and oxidation of lipids, which may be detected in a sample by, for example, measurement of alkenals such as 4-hydroxynonenal (4HNE). In particular, herein the term "placental oxidative stress" refers to oxidative stress occurring in the placenta. Whilst not wishing to be bound by theory, the inventors propose that increased oxidative stress in the placenta is related to ageing of the placenta and may result in deficiencies in the placenta's ability to adequately sustain a fetus. The inventors hypothesise that oxidative stress in the placenta may therefore be associated with increased risk of stillbirth.

The term "biomarker" as used herein refers to a naturally occurring, biologically functional compound or molecule, such as a gene, nucleic acid sequence, protein or fragment thereof, or other metabolite that has predictive value for the diagnosis of tissue aging in a variety of body tissue, such as placenta, skin, kidney and brain, for the diagnosis of preeclampsia, for the diagnosis of intra-uterine growth restriction, and for the diagnosis and assessment of risk of post-dated pregnancy and stillbirth. Determination of the level or activity of a marker in a biological sample may comprise the detection and quantitation of the marker itself or of a precursor, derivative or metabolite thereof. The terms "biomarker" and "marker" may be used interchangeably herein.

In the context of the present disclosure, the biomarker may be an RNA or other nucleic acid sequence. In embodiments in which placental tissue aging, and related conditions and effects are assessed, the mRNA may be derived from the placenta and measured in maternal blood. Also in accordance with embodiments of the present disclosure is the determination of expression of precursors, derivatives, variants, analogues and functional fragments of biomarkers identified herein. A variant of a biomarker includes a molecule that exhibits at least some of the functional activity of the biomarker of which it is a variant.

In the context of the present disclosure, reference to an increase in expression of a marker in a given sample means an increase in the level of expression of the marker in question in the sample, typically when compared to the expression levels in one or more control or reference samples or when compared with a baseline measurement of the sample in the same subject. Control or reference samples may be used herein to indicate samples obtained from one or more individuals with no signs of oxidative stress or tissue ageing and/or, in the case of pregnant individuals, not at risk of post-dated pregnancy or stillbirth.

In one aspect the present disclosure provides a method for detecting or determining aging in body tissue, the method comprising measuring one or more markers of aldehyde oxidase 1 (AOX1) expression or activity in a biological sample obtained from a subject, wherein the level of AOX1 expression or activity, as determined by the level(s) of the one or more markers, is indicative of aging in the tissue.

A further aspect of the present disclosure provides a method for detecting placental aging, the method comprising obtaining a biological sample from a pregnant subject and measuring one or more markers of placental AOX1 expression or activity in the biological sample, wherein the level of AOX1 expression or activity or of the one or more markers thereof is indicative of placental aging. A further aspect provides a method for predicting the risk of stillbirth in a pregnancy, the method comprising obtaining a biological sample from a pregnant subject and measuring one or more markers of placental AOX1 expression or activity in the biological sample, wherein the level of AOX1 expression or activity, or of the one or more markers thereof, is indicative of risk of stillbirth.

The inventors' novel findings as disclosed and exemplified herein provide, in some embodiments, an accurate, cost effective, rapid methodology for predicting the risk of post-dated pregnancy or stillbirth. Thus, in exemplary embodiments, disclosed herein is a simple biochemical test that facilitates the prediction of risk of stillbirth and the identification of therapeutic preventative or prophylactic regimes for at risk pregnancies.

The inventors' novel findings as disclosed and exemplified herein also provide, in some embodiments, accurate, cost effective, rapid methodologies for detecting or determining tissue aging and for detecting or determining tissue oxidative damage, in a range of body tissues, including for example placental, skin, kidney and brain tissue.

The inventors demonstrate herein that between 38 and 41 weeks of gestation dramatic changes occur in the biochemistry and physiology of the placenta. In particular there is increased oxidative damage to DNA and lipid, change in position of lysosomes which accumulate at the perinuclear and basal surface of the syncytiotrophoblast, the formation of larger autophagosomes which are associated with oxidised lipid and there is increased expression of the enzyme AOX1. The same changes are observed in placentas associated with stillbirth. Similar changes in oxidation of lipid, localisation of lysosomes and size of autophagosomes occur in placental explants deprived of growth factors and these changes can be blocked by inhibition of AOX1.

The inventors also demonstrate herein that the physiological function of the placenta at 41 weeks shows evidence of decline that has many features of aging in other tissues. The known exponential increase in unexplained intrauterine death that occurs after 38 weeks of gestation may therefore be a consequence of aging of the placenta and decreasing ability to function adequately to supply the increasing needs of the growing fetus. This knowledge may impact on obstetric practice to ensure infants are born before the placenta ages to the point of critical failure.

As has been noted hereinbefore, the risk of stillbirth increases with gestational age, and in particular rises exponentially as gestation progresses beyond 38 weeks. Similarly, signs of oxidative damage increase as the placenta ages. However those skilled in the art will recognise that signs of placental aging, and therefor of oxidative damage, may appear at different times, and progress at different rates, in different individuals. Thus, one cannot prescribe a specific gestational age at which, or from which, methods of the present invention should be initiated, nor the number of times during pregnancy that a method should be employed. For example, a method of the present disclosure may be carried out from approximately 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks or 41 weeks gestation in the case of a human subject. The method may be carried out one or more times during pregnancy, for example every week or every two weeks. The frequency of testing and monitoring using methods disclosed herein may increase as gestational age increases. The appropriate timing for initiation of testing and monitoring in accordance with the present disclosure, and the appropriate frequency, can be determined on a case to case basis by the skilled addressee without undue burden or the need for further invention.

The inventors also demonstrate herein that their findings extend to tissue other than placental tissue, providing evidence that AOX1 causes oxidative damage in the kidney.

Without wishing to be bound by theory, the inventors suggest that increased AOX1 expression or activity in tissue, such as placenta, skin, kidney or brain, leads to oxidative damage and oxidative stress in the tissue and contributes to tissue aging (FIG. 1, in the context of the placenta). In the case of placental tissue, aging of the placenta may result in lack of delivery of appropriate nutrients to the fetus, causing intra-uterine growth restriction and/or stillbirth. The inventors have shown that indicators of placental oxidative stress, such as placental aldehyde oxidase, can be measured in maternal blood providing a biomarker of placental integrity that may be assayed non-invasively, with minimal risk to the fetus. Accordingly, disclosed herein are suitable methods for assaying the risk of stillbirth in a pregnancy using biomarkers of placental oxidative stress, such as AOX1 expression. The inventors also demonstrate that such oxidative stress may be prevented with AOX1 inhibition.

The inventors also note that indicators of placental aging, such as oxidative damage and lysosomal localisation, are shared with other pathologies such as Alzheimer's disease, and suggest that aging and oxidative stress in general may be associated with AOX1 and may also be delayed or prevented with AOX1 inhibition.

In particular embodiments of the present disclosure, the methods comprise measurement of placental AOX1 mRNA in maternal blood. Additional placental oxidative stress biomarkers, as surrogates for AOX1 expression or activity, include, but are not limited to: lipid peroxidation products such as 4-hydroxynonenal (4HNE) and other hydroxyalkenals, which are indicative of oxidative damage to lipids; 8-hydroxyguanosine (8OHdG) and 8-hydroxy guanosine (8HOG) which are indicative of oxidative damage to nucleic acids; and other markers indicative of oxidative stress, such as malondialdehyde (MDA), isoprostanes, oxysterols or increased protein carbonyl concentration.

Embodiments of the disclosure comprise methods for detecting and determining risk of post-dated pregnancy and stillbirth, wherein an increase in AOX1 mRNA or other marker of AOX1 expression or activity above a baseline (as typically determined by one or more reference values as described hereinbefore) is indicative of placental oxidative stress and increased risk of post-dated pregnancy or stillbirth. As stillbirth can occur at any stage of pregnancy (by definition more than 20 weeks gestation or 400 g in humans), methods disclosed herein contemplate monitoring the presence and level of oxidative stress markers disclosed herein in total maternal blood at various time points through a pregnancy. Such markers may be detected and measured from, in a human for example, 20 weeks gestation and at 1, 2, 3 or 4 week intervals over the course of the pregnancy. An increase in AOX1 mRNA or marker of AOX1 expression or activity from baseline will be indicative of increased risk of post-dated pregnancy or stillbirth.

Biochemical tests used to determine biomarker levels in accordance with embodiments disclosed herein may be carried out utilising any means known in the art and the present disclosure is not limited by reference to the means by which the biomarker levels are determined. Determination of biomarker levels may comprise detection and/or quantitation and the methods and techniques available for such determination are well known to those skilled in the art. Typically, if the biomarker is an mRNA, an assay of the present disclosure will be quantitative real-time PCR. Other methods of detecting biomarkers of the present specification include but are not limited to PCR, DNA array, microarray, ligase chain reaction, oligonucleotide ligation assay, cDNA microarray, next generation sequencing, northern blotting, in situ hybridisation and further statistical analysis to determine differential expression in an individual.

Suitable methods and techniques for measuring protein biomarkers may also include, but are not limited to, the use of spectral analysis, column chromatography, gel electrophoresis, mass spectroscopy and identification of protein spots, enzyme-linked immunosorbent assay (ELISA), Western blot, image acquisition and analysis (such as magnetic resonance imaging (MRI) spectroscopy and single photon emission computed tomography (SPECT)), immunostaining, HPLC, LC/MA. Biochemical tests used to determine biomarker levels in accordance with embodiments disclosed herein may be employed in any suitable environment or setting, such as a hospital, clinic, surgical or medical practice, or pathology laboratory.

Suitable biochemical tests may be incorporated into one or more devices capable of analysing the desired biomarkers to thereby allow a degree, or complete, automation of the testing process. Suitable devices are typically capable of receiving a biological sample, analysing one or more biomarker levels in said sample and providing data on said biomarker level(s) in real time thus facilitating bench-to-bedside and point-of-care analysis, diagnosis, risk assessment and/or treatment. It should be understood that reference to determining the level of expression or level of a marker is intended as a reference to the use of any suitable technique that will provide information in relation to the level of expression or level of the desired marker in the relevant tissue of the subject. Accordingly, these techniques include both in vivo techniques such as MRI imaging with phosphorous coils, as well as in vitro techniques that are applied to a biological sample extracted from the subject. Other oxidative stress markers, such as 4HNE, 8OHdG or 8HOG may be detected by methods well known in the art, such as by fluorescent detection, immunohistochemical or chromatographic methods such as HPLC.

Biological samples obtained from an individual to determine oxidative stress marker levels may be derived from any suitable body fluid or tissue. Typically, in methods of the disclosure, the sample may comprise blood (such as erythrocytes, leukocytes, whole blood, blood plasma or blood serum), urine, amniotic fluid, saliva or tissue. If the subject is pregnant, the biological sample may be of maternal, placental or fetal origin. In an embodiment, the biological sample is maternal total blood.

It is known in the art that fetal cells or nucleic acids may be present in maternal blood. The biomarkers measured in the methods of this disclosure may therefore be measured in samples such as free DNA or free RNA, placental cells, fragments of placental cells, exosomes or microparticles that are released from the placenta into the maternal circulation.

If increased AOX1 mRNA or biomarker levels are detected prior to naturally occurring labour a physician may consider available options to reduce stillbirth risk. Such options include, for example, induction of labour or caesarean section if the fetus is at a stage where it is likely to be viable when born. If increased AOX1 mRNA or biomarker levels are detected at an age where the infant would be considered pre-term, options may be considered to delay placental ageing or prolong the gestation. As disclosed and exemplified herein, options may include, for example, treating the pregnant mother with an antioxidant treatment or one or more AOX1 inhibitors. As further discussed hereinbelow, examples of appropriate AOX1 inhibitors include raloxifene or agonists of G protein-coupled estrogen receptor 1 (GPER1), such as G-1.

Embodiments of the disclosure provide that markers of AOX1 expression or activity may be determined or measured in combination with one or more clinical assessments as further indicators of tissue aging. For example, in a pregnant subject, clinical assessments such as altered fetal movements, measures of fetal growth or altered Doppler studies of the placental arteries, placental veins or the fetal cerebral artery may be used in combination with markers of AOX1 expression or activity to assessing placental aging, risk of stillbirth, need for intervention to prevent stillbirth and placental oxidative stress. Clinical assessments appropriate to the context may readily be determined by a person skilled in the art.

The present disclosure also provides kits suitable for use in accordance with the methods of the disclosure. Such kits include, for example, prognostic kits for assaying biological samples comprising reagents for detecting expression levels of discriminatory biomarkers disclosed herein (such as AOX1 mRNA, 4HNE, 8HOG and 8OHdG). Kits according to the present disclosure may also include other components required to conduct the methods of the present disclosure, such as buffers and/or diluents. The kits typically include containers for housing the various components and instructions for using the kit components in the methods of the present disclosure.

The present disclosure also contemplates the administration of therapeutic agents to arrest oxidative damage or tissue aging. In some embodiments, suitable therapeutic agents may be administered during pregnancy in the case of placental oxidative damage or placental aging in a pregnancy identified at high risk of stillbirth, including when extreme prematurity precludes delivery. Without wishing to be bound by theory, the inventors suggest that the placenta may provide a tractable model of aging in a human tissue that uniquely ages in a 9 month period of time. Herein, the inventors demonstrate changes in placental oxidative stress markers and lysosomal positioning that are similar to changes in ageing diseases, such as Alzheimer's disease and Huntington's disease (see Examples). Similarities in oxidative damage and lysosymal distribution between placental aging and aging in neurodegenerative diseases suggest that there may be a similar mechanism of aging in these conditions. It is therefore contemplated in the present disclosure that ageing due to oxidative stress and diseases and conditions in which oxidative damage is pathological may be prevented, delayed or treated with administration of AOX1 inhibitors, such as GPER1 agonists or raloxifene, and other inhibitors of AOX1 or GPER1 agonists as contemplated herein.

Accordingly, in other embodiments, suitable therapeutic agents may be administered to prevent, delay, slow, retard or treat aging and oxidative stress or damage in skin, kidney or brain tissue. Oxidative stress and damage in such tissues may be merely the result of the aging process, or may be caused, accelerated or exacerbated by a range of other factors. By way of example only, oxidative damage and aging of the skin may be associated with prolonged exposure to the sun or sunburn, oxidative damage and aging of the kidney may be associated with acute or chronic kidney injury or disease, smoking and drug abuse, hypertension, dyslipidemia, obesity and inflammatory disorders, and oxidative damage and aging of the brain may be associated with brain injury or trauma or a neurodegenerative condition such as memory loss, Alzheimer's disease and Parkinson's disease.

According to methods of the present disclosure, therapeutic agents for use in accordance with the present disclosure include, for example, inhibitors of AOX1, including but not limited to raloxifene and G protein-coupled receptor 1 (GPER1) agonists. For example, in embodiments of the disclosure, agonists of GPER1 may be used to reduce or prevent oxidative stress in the placenta. One particularly suitable agonist of GPER1 for use in accordance with the present disclosure is G-1, (1-[4-(6-bromobenzo[1,3] dioxol-5yl)-3a,4,5,9b-tetrahydro-3H-cyclcopenta[c]quinolin-8-yl]-ethanone). G-1 is a cell-permeable, nonsteroidal, dihydroquinoline compound that acts as a high-affinity GPER agonist.

However those skilled in the art will appreciate that the scope of the present disclosure is not so limited, and any other AOX1 inhibitor or an agent capable of activating, directly or indirectly, the GPER1 receptor or its downstream pathways may be employed. Other inhibitors of AOX1 also suitable for use in methods of the disclosure may, for example, include tamoxifen, estradiol, ethinyl estradiol, phenothiazines, tricyclic antidepressants, tricyclic atypical antipsychotics, dihydropyridine calcium channel blockers, loratidine, cyclobenzaprine, amodiaquine, maprotiline, ondansetron, propafenone, domperidone, quinacrine, ketoconazole, verapamil, tacrine and salmeterol.

Additional therapies that may be used in conjunction with, or in place of, the therapeutic compounds targeting GPER1 or AOX1 include antioxidant molecules, compounds or treatments, for example thiols, ascorbic acids or phenols (such as polyphenol), superoxide dismutase, catalase, peroxiredoxin, thioredoxin, glutathione, carotenes, alpha-tocopherol, resveratrol and flavonoids.

For the purposes of the present disclosure compositions comprising therapeutic agents for administration may be prepared by methods well known to those skilled in the art. Accordingly, the compositions may comprise pharmaceutically acceptable carriers, diluents, excipients and/or adjuvants. The carriers, diluents, excipients and adjuvants must be "acceptable" in terms of being compatible with other components of the composition, and not deleterious to the subject who is to receive the composition. The pharmaceutically acceptable carriers, diluents, excipients and/or adjuvants to be used may depend on the intended route of administration of the composition and will be well known to those skilled in the art. Compositions may be administered via any convenient or suitable route, including for example, topical, oral, nasal or other mucosal route, or parenteral, such as subcutaneous, intramuscular, or intra-arterial. The route of administration will depend on a number of factors, including the tissue to which the treatment is directed. Similarly the form or vehicle in which the composition is administered will depend on a number of factors, including the tissue to which the treatment is directed. Exemplary forms may include injectable solutions or suspensions, lotions, liniments, gels, creams, ointments, foams, oils, powders and the like for topical administration, and tablets, troches, capsules, elixirs, suspensions, syrups, wafers, granules, powders, gels, pastes, solutions, suspensions, soluble sachets, caplets, lozenges, effervescent tablets, chewable tablets, multi-layer tablets, and the like for oral administration.

In one exemplary embodiment for the administration of a composition for treating, preventing, slowing, retarding or delaying skin aging or oxidative damage in the skin, a suitable AOX1 inhibitor or GPER agonist as disclosed herein may be formulated into a liniment, gel, cream, ointment, foam, oil, or the like for topical application to the skin. Such a formulation may be applied directly to the skin, or may be applied by adding the formulation to a bath. The formulation may also comprise, for example, a sunscreen, vitamin E or other suitable ingredient to minimise the effect of UV radiation and/or assist with skin moisturisation and/or repair.

Examples of pharmaceutically acceptable carriers, diluents, excipients and adjuvants include, but are not limited to, demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure will now be described with reference to the following specific examples, which should not be construed as in any way limiting the scope of the disclosure.

EXAMPLES

The following examples are illustrative of the disclosure and should not be construed as limiting in any way the general nature of the disclosure of the description throughout this specification.

General Methods

Ethics, Collection and Processing of Tissues

This study was approved by the human research ethics committee of the Hunter New England Health Services and the University of Newcastle, NSW, Australia. Human placentas were collected after written informed consent was obtained from the patients by midwives. Placentas were collected from women at 38-39 weeks (term) gestation undergoing caesarean section for previous caesarean section and having normal vaginal delivery and women at 41$^+$ weeks gestation undergoing caesarean section and having normal vaginal delivery and women who had stillborn infants undergoing vaginal delivery. Placentas were collected immediately after delivery and processed without further delay. Villous tissues were sampled from multiple sites and were prepared for histology and RNA extraction. For each placenta, tissues were obtained from at least 5 different regions of the placenta and 4-5 mm beneath the chorionic plate. Samples from each individual placenta were immediately frozen under liquid nitrogen and stored at −80° C. until subsequent experiments. For histology experiments, tissues were fixed in 2% formaldehyde for 24 hr, stored in 50% ethanol at room temperature (RT) and embedded in paraffin. To create a placental roll a 2 cm strip of chorio-amniotic membrane was cut from periphery of the placenta keeping a small amount of placenta attached to the membrane. The strip was rolled around forceps leaving residual placenta at the centre of the cylindrical roll. The cylindrical roll was then cut perpendicular to the cylindrical axis to get 4 mm thick section. The tissue was then fixed in formalin and mounted in a paraffin block. Placentas from patients with infection, diabetes, pre-eclampsia, placenta praevia, intra-uterine growth restriction or abruption were excluded.

Placental Explant Culture

For in vitro experiments, human term placentas (38-39 weeks of gestation) were obtained from women with normal singleton pregnancies without any symptoms of labour after an elective (a scheduled repeat) caesarean section. Placentas were collected immediately after delivery and prepared for explant culture. Villous tissues of placentas were randomly sampled from different regions of placenta and 4-5 mm beneath the chorionic plate. Tissues were washed several times with Dulbecco's phosphate-buffered saline (DPBS) under sterile condition to remove excess blood. Villous explants of ~2 mm$^3$ were dissected and placed into 100×20 mm culture dishes (30 pieces/dish) containing 25 ml of Dulbecco's modified Eagle's medium (DMEM) supplemented with 2 mM L-glutamine, 1% Na-pyruvate, 1% penicillin/streptomycin (100×) solution with the addition of 10% (v/v) fetal bovine serum (FBS) and were cultured in a cell culture chamber at 37° C. temperature and maintaining 95% air (20% oxygen) and 5% $CO_2$ for 24 hours. At day 2, villous explants were transferred to fresh 30 ml growth medium and incubated in a cell culture chamber for 90 minutes. After this the tissues were washed in DMEM without FBS (refer to as 'serum-free medium' or 'growth factor deficient medium'). Next 6-7 pieces of villous tissue weighing approximately 400 mg were transferred to a culture dish (60×15 mm) containing 6 ml serum-free medium with or without the addition of pharmacological agents, for example, raloxifene (1 nM) and GPER1 agonist G1 (1 nM), for subsequent incubation up to 24 h. At the end of 24 h some tissues were fixed in 2% formaldehyde, subjected to routine histological processing and embedded in paraffin wax, and some tissues were immediately frozen in liquid nitrogen and stored at −80° C. until subsequent experiments. For each placental explant culture, samples were also collected at time '0 (zero)' h i.e., before incubation in serum free medium, and were formalin fixed and stored frozen at −80° C. until further experiments.

Western Blotting

Western blotting was performed according to Maiti, K et al (2011, *Endocrinology*, 152:2448-2455). Samples of placenta (1 g) were crushed under liquid nitrogen. Aliquots of 100 mg of placental tissues were homogenised in 1 mL of lysis buffer (phosphate buffered saline (PBS), 1% Triton-X-100, 0.1% Brij-35, 1× protease inhibitor, 1× phosphatase inhibitor, pH 7.4). The protein concentration of each placental extract was measured using a BCA protein determination kit and 40 µg of placental extract was separated by electrophoresis in NuPage bis-tris precast 12 well gels for 50 mins at constant 200 V. Separated proteins were then transferred to nitrocellulose membrane using a Novex transfer system for 70 mins and blocked overnight with 1% bovine serum albumin (BSA) in tris buffered saline with 0.1% tween-20 (TBST). The membranes were then incubated with primary antibody in 1% BSA in TBST for 2 hours, then washed three times with TBST, then incubated with HRP conjugated secondary antibodies in 1% BSA in TBST for an hour. After three further washes with TBST, the immunoreactive bands were developed in Luminata reagent and detected using an Intelligent Dark Box LAS-3000 Imager (Fuji Photo Film, Tokyo, Japan).

Detection of 4HNE in Maternal Plasma

For detection and quantitation of 4HNE protein adduct in maternal plasma, the inventors used an OxiSelect™ HNE Adduct Competitive ELISA Kit (Cell Biolabs Inc, STA-838). This assay is based on the competition between HNE conjugate and the anti-HNE antibody for HNE-protein. In this assay, at first, an HNE conjugate is coated on an ELISA plate. The unknown HNE protein samples or HNE-BSA standards are then added to the HNE conjugate reabsorbed ELISA plate. After a brief incubation, an anti-HNE antibody is added, followed by a secondary antibody (HRP conjugated). The amount of HNE protein adducts in unknown samples is estimated from a predetermined HNE-BSA standard curve.

In this assay, at first, an HNE conjugate was coated on a 96-well plate and incubate overnight at 4° C. HNE conjugate was removed, and the wells were rinsed twice with 1× PBS. Assay Diluent was added to each well and blocked for an hour at RT and then transferred to 4° C. until use. Immediately before use, Assay Diluent was removed and 50 µl maternal plasma samples and HNE-BSA standards were added. The plate was then incubated for 10 min at RT on an orbital shaker. The diluted anti-HNE antibody was added to each well and incubated at RT for 2 hours on an orbital shaker. The plate was then washed 3 times with 1× wash buffer with thorough aspiration between each wash. The diluted HRP conjugated secondary antibody was added to all wells and incubated for an hour at RT on an orbital shaker. The strip wells were then washed a further 3 times with 1× wash buffer. The substrate solution was added to each well, incubated at RT for 2-5 minutes on an orbital shaker and the changes of colour were monitored. The stop solution was added to each well to stop the enzyme reaction. The absorbance of each well was read on a microplate reader (SPECTROstar Nano, BMG LABTECH) using 450 nm as the primary wavelength. The content of HNE protein adducts in unknown samples was determined by comparison with the predetermined HNE-BSA standard curve using GraphPad Prism software. The results were graphed, and the statistical analysis was performed using GraphPad Prism software.

Immunohistochemistry

6 µm paraffin placental sections were deparaffinised and hydrated, then heated with tris-EDTA buffer (pH 9) in a microwave oven for antigen retrieval. The sections were blocked with 1% BSA in TBST for an hour at room temperature. The sections were incubated with primary antibodies overnight and washed three times with TBST, before incubation with Alexa-conjugated secondary antibodies for 90 mins. The sections were mounted with antifade solution with DAPI. The fluorescent photographs for FIGS. 3 to 7, 9 and 11 were taken on a Nikon eclipse 90i confocal microscope. The fluorescent photographs for FIG. 10 were taken on Nikon eclipse Ti fluorescence microscope.

RNA Isolation and Real Time PCR

Placental tissues were crushed under liquid nitrogen. Approximately 100 mg of crushed placental tissues were homogenised in 2 ml of Trizol reagent by Ultra Turrax homogenizer. Total RNA was extracted from Trizol-extract by Direct-zol™ RNA MiniPrep. The RNA was treated with DNAse and purified with a RNA Clean & Concentrator™-5 kit. The RNA quality was observed by running the DNAse treated sample in agarose gel with ethidium bromide in 1× TAE buffer. The purified RNA was used to make cDNA using a SuperScript® III First-Strand Synthesis System kit. The cDNA was used to run real time PCR by Taqman primers for aldehyde oxidase 1 (AOX1) and Taqman gene expression master mix with an internal control 18 s ribosomal RNA to quantify mRNA for AOX1. SyBr green master mix was used to quantify mRNA for G-protein coupled receptor 1 (GPER1) with respect to beta-actin as internal control using the Applied Biosystem 7500 PCR system.

GPER1 primers were 5'-CGTCCTGTGCACCTT-CATGT-3' (forward, SEQ ID NO. 1) and 5'-AGCT-CATCCAGGTGAGGAAGAA-3' (reverse, SEQ ID NO. 2). AOX1 primers were obtained from Thermo-fisher Scientific (CAT: 4331182, assay number: Hs00154079_m1). The AOX1 TaqMan assay was designed to detect an 84 bp amplicon from base 3270 of NM_001159.3 (herein SEQ ID NO. 3), at the exon 27/28 boundary.

Statistical Analysis

Sample numbers are shown in the legends to individual figures. The data in FIGS. 3, 4, 6, 9 and 12 were analysed by using the Mann-Whitney test (two way) and results are presented as scatter plots showing the median or standard error of the mean. The data in FIGS. 10 and 11 were analysed using the Wilcoxon matched-pairs signed rank test. All the p-values were calculated using the Graphpad Prism software.

Example 1—Relationship Between Stillbirth Risk and Length of Gestation

Figure 2:
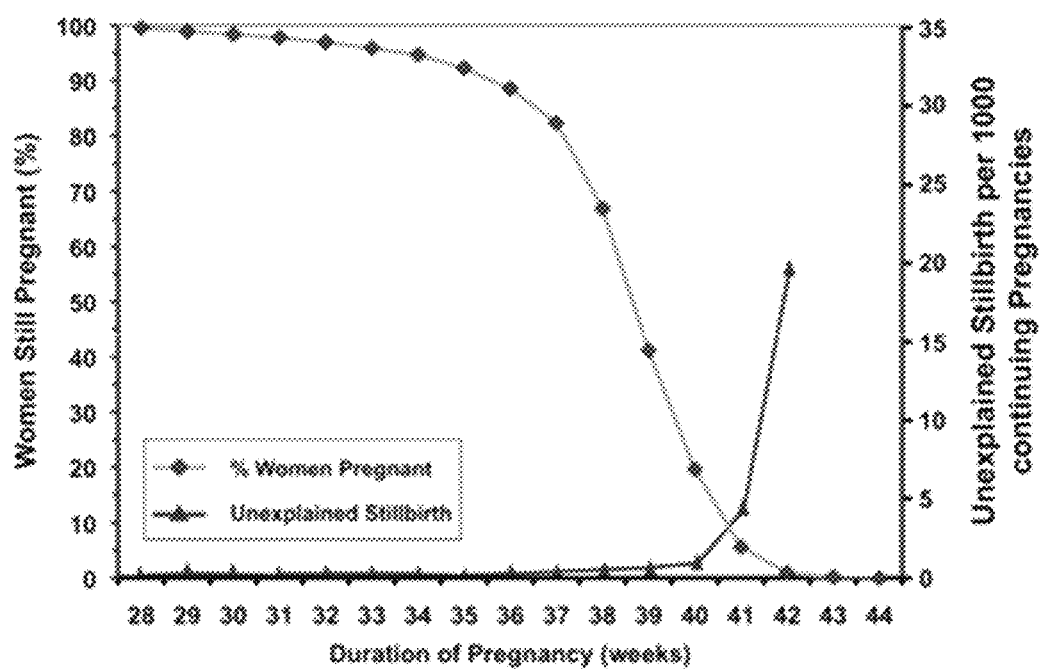
FIG. 2: Relationship between stillbirth and number of continuing pregnancies. Kaplan Myer plot of number of continuing pregnancies as a function of gestational age and plot of unexplained stillbirths per 1000 continuing pregnancies; data from Omigbodun and Adewuyi (1997) (*J Natl Med Assoc,* 89: 617) and Sutan et al. (2010) (*J Perinatol,* 30: 311-318). Plot shows the increase in risk of stillbirth with time consistent with the operational definition of aging proposed by Johnson et al (1999) (*Cell,* 96: 291-302) and the relatively small number of pregnancies at risk of stillbirth by 41 weeks because of prior delivery.

To illustrate the relationship between stillbirth risk and length of gestation the inventors created a Kaplan Myer plot of the data on human gestational length in a population with relatively low levels of medical intervention from Omigbodun and Adewuyi (1997, *J Natl Med Assoc*, 89: 617) and combined it with the data on risk of stillbirth per 1000 continuing pregnancies from Sutan et al. (2010, *J Perinatol*, 30: 311-318) (FIG. 2). The data illustrate that stillbirth is consistent with an aging aetiology as defined by Johnson et al. (1999, *Cell*, 96: 291-302).

Example 2—DNA/RNA and Lipid Oxidation in Placental Tissue

Figure 3:
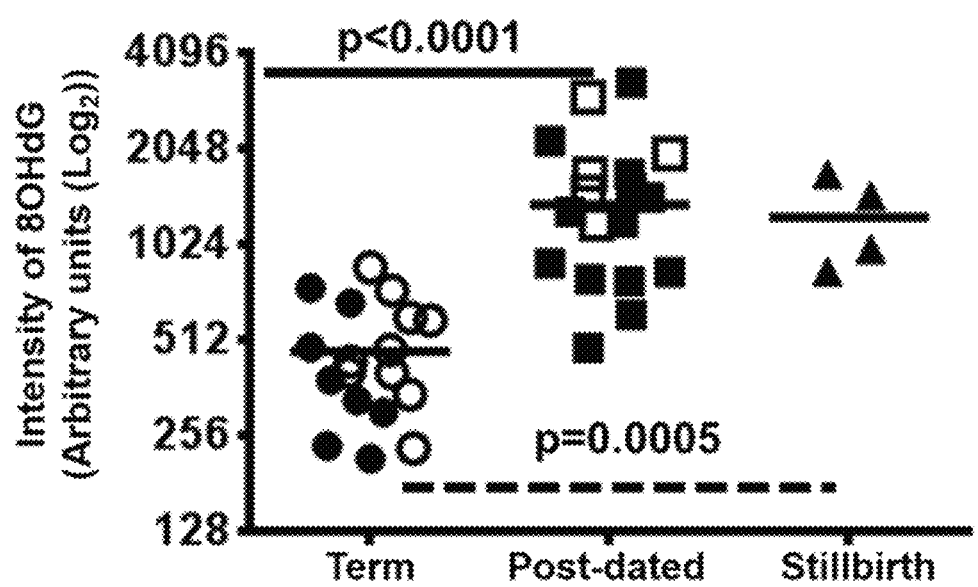
FIG. 3: DNA/RNA oxidation in post-dated and stillbirth placentas. The graph illustrates that post-dated and stillbirth placentas have increased intensity of nuclear 8OHdG/8HOG staining ($p<0.0001$ for post-dated placentas, $p=0.0005$ for stillbirth placentas, Mann Whitney test) compared to term placentas. Open circles and filled circles represent term caesarean non-labouring placentas (n=10) and term vaginal delivery labouring placentas (n=8), respectively. Open squares and filled squares represent post-dated labouring caesarean placentas (n=5) and post-dated labouring vaginal delivery placentas (n=13), respectively. Filled triangles represent third trimester labouring vaginal delivery unexplained stillbirth placentas (n=4). Each point in the graph represents the average intensity of 8OHdG/8HOG of 60 nuclei in 6 images per placenta photographed at 100× magnification and 1.4 optical resolution.
Figure 4:
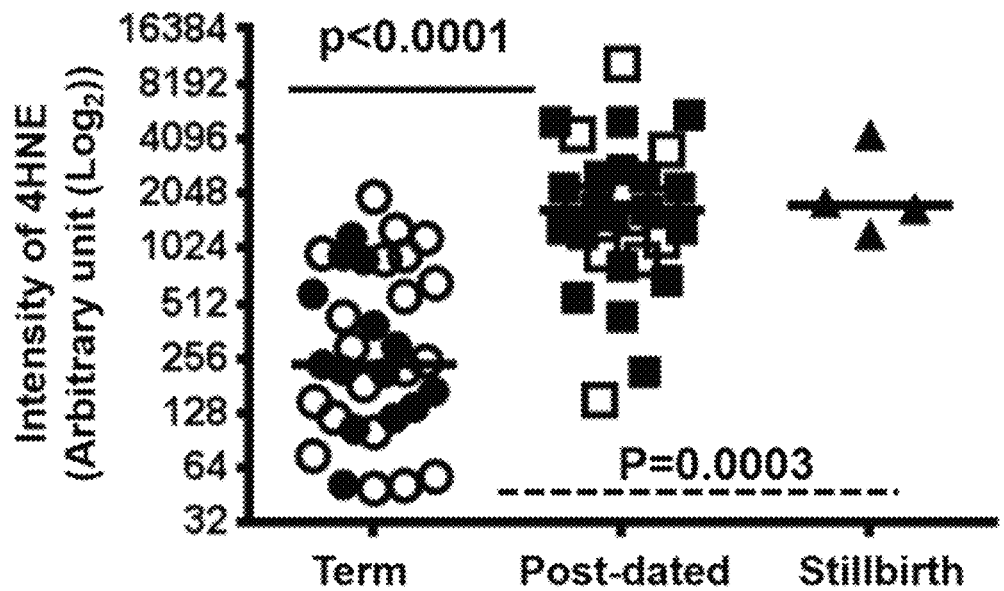
FIG. 4: Lipid peroxidation is increased in post-dated and stillbirth placentas. The intensity of 4HNE is significantly increased in post-dated placentas ($p<0.0001$, Mann Whitney test) and stillbirth placentas ($p=0.0013$, Mann Whitney test). Open circles and filled circles represent term caesarean non-labouring placentas (n=21) and term vaginal delivery labouring placentas (n=14), respectively. Open squares and filled squares represent post-dated labouring caesarean placentas (n=10) and post-dated labouring vaginal delivery placentas (n=18), respectively. Filled triangles represent third trimester labouring vaginal delivery unexplained stillbirth placentas (n=4). Each point in the graph represents the mean intensity per unit area for 6 images taken for each individual placenta photographed at 100× magnification and 1.4 optical resolution.

As oxidative damage has been observed in many aging tissues, the inventors sought evidence of placental DNA/ RNA oxidation as measured by 8-hydroxy-deoxyguanosine/ 8-hydroxyguanosine (8OHdG/8HOG), as a marker of DNA/ RNA oxidation. Immunohistochemistry (IHC) was performed in placentas for 8OHdG/8HOG and the average intensity of 8OHdG/8HOG staining in nuclei/frame demonstrated a significant increase in DNA/RNA oxidation in post-dated and stillbirth associated placentas (FIG. 3).

The increase in DNA oxidation suggested free radical damage that might also lead to lipid peroxidation. Lipid peroxidation has been observed to increase in Alzheimer's disease as measured by the formation of 4-hydroxynonenal (4HNE) (Markesbery and Lovell, 1998, *Neurobiol Aging*, 19: 33-36). The inventors therefore performed immunohistochemistry for 4HNE in post-dated, stillbirth and term placental tissue. This revealed a marked increase in 4HNE staining in post-dated syncytiotrophoblasts that was also observed in placentas associated with stillbirth shown in FIG. 4. High levels of 8OHdG/8HOG and 4HNE in post-dated and stillbirth placentas suggest that placental aging may have occurred in these placentas.

Figure 5:
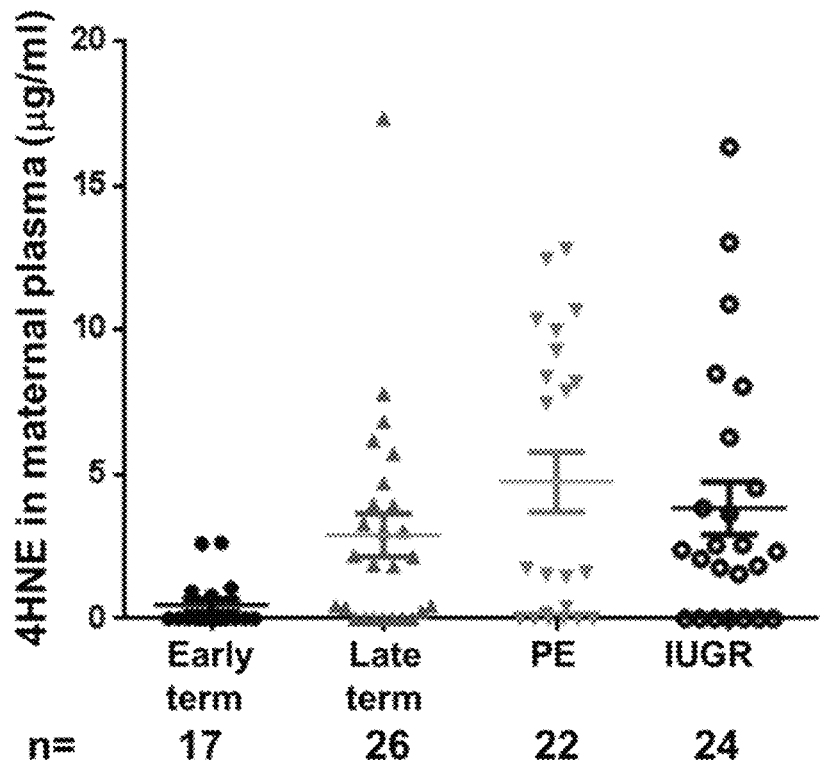
FIG. 5: Levels of 4HNE in maternal plasma from early term (n=17), late term (n=26), pre-eclamptic (PE, n=22) and intrauterine growth restriction (IUGR, n=24) cases. The late term, PE and IUGR groups have significantly higher levels of 4HNE than early term. Early term v late term, $p=0.0016$; early term v PE, $p=0.0017$; early term v IUGR, $p=0.0016$.
Figure 6:
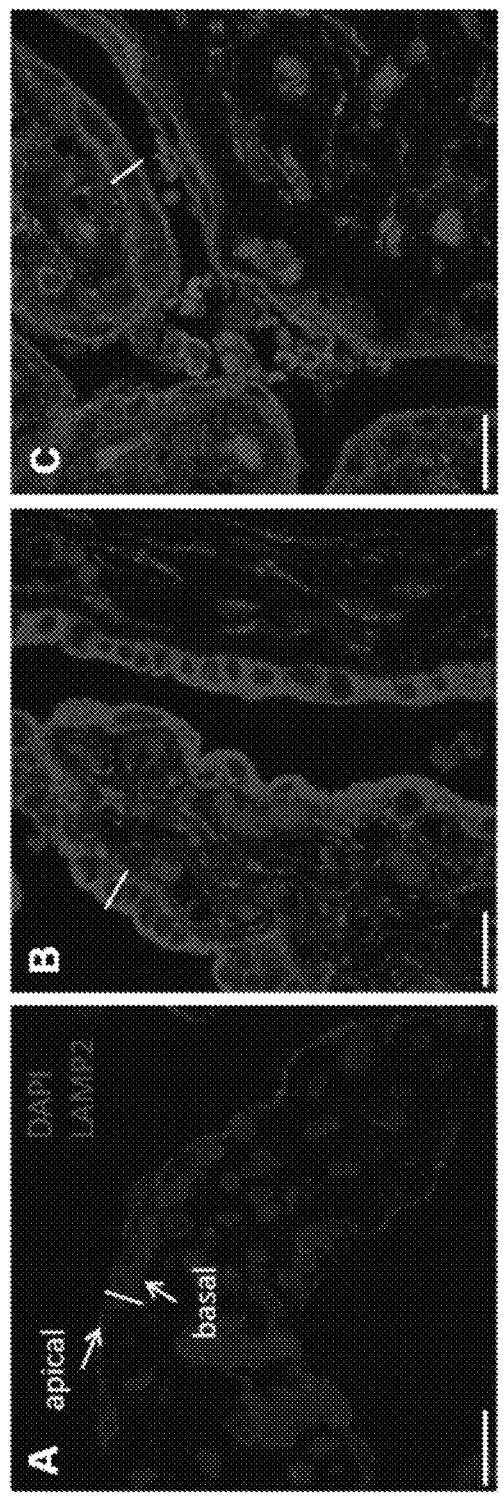
FIG. 6: Changes in lysosomal distribution in post-dated and stillbirth placentas. Immunohistochemistry of LAMP2, a lysosomal marker showed that lysosomes predominantly localise to the apical surface of term placentas (A), whereas lysosome distribution extends to the perinuclear and basal surface of syncytiotrophoblast in post-dated (B) and stillbirth placentas (C) (e.g. as designated by white lines). Intensity calculation across the syncytiotrophoblast showed that the distribution of LAMP2 in post-dated (n=5, FIG. 5F) and unexplained stillbirth placentas (n=4, FIG. 5G) shifts to the perinuclear and basal surface whereas lysosome distribution in term caesarean placentas (n=5, FIG. 5D) and term vaginal delivery placentas (n=5, FIG. 5E) remained in the apical region of the syncytiotrophoblast. DAPI staining identifies the nuclei.
Figure 6:
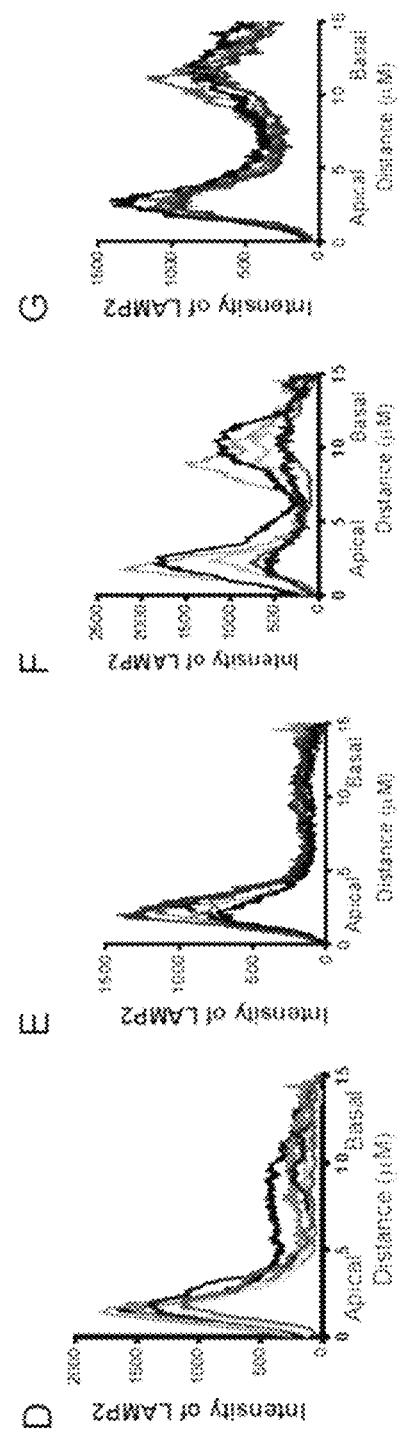

The inventors also investigated 4HNE levels in maternal plasma, using a commercial ELISA kit, in cases of early term birth, late term birth (post date delivery), pre-eclampsia and intra-uterine growth restriction (IUGR). 4HNE levels were found to be significantly higher in each of the post date delivery, pre-eclampsia and IUGR cases when compared to early term (FIG. 5). Post date delivery, pre-eclampsia and IUGR are all known to be associated with increased risk of stillbirth.

Example 3—Movement and Clustering of Lysosomes in Post-Dated and Stillbirth Placentas Misfolded proteins and damaged mitochondria are normally recycled in autophagosomes in a process that involves autophagosome fusion with proteolytic enzyme containing lysosomes. Accumulation of abnormal protein is thought to play a role in aging particularly in the brain, for instance the accumulation of tau and amyloid protein in Alzheimer's disease and mutant huntin in Huntington's disease. In Huntington's disease, the distribution of the lysosomes within neurones is altered with increased perinuclear accumulation of lysosomes. The inventors used a lysosomal marker, lysosome-associated membrane protein-2 (LAMP2) to analyse the distribution of lysosomes in the placenta by immunohistochemistry. This showed lysosomes positioned on the apical surface of term placental syncytiotrophoblast (FIGS. 6A, 6D and 6E), whereas lysosomes relocated to the perinuclear and the basal surface in post-dated and stillbirth placentas (FIGS. 6B, 6C, 6F and 6G).

The present data demonstrate marked accumulation of particles positive for the lysosomal marker LAMP2 in the perinuclear and basal side of the syncytiotrophoblast of post-dated placentas and placentas associated with stillbirth.

Figure 7:
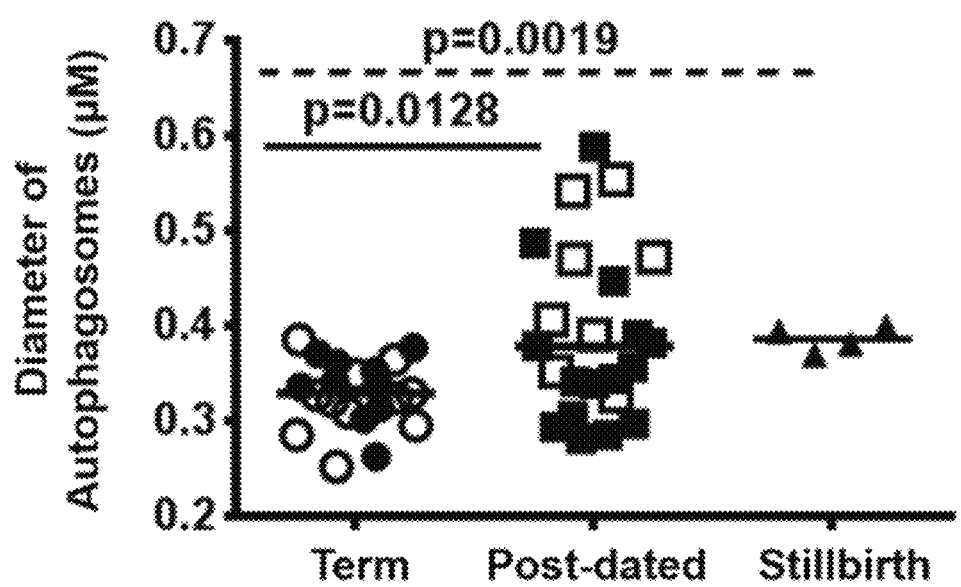
FIG. 7: Larger autophagosomes occur in post-dated and stillbirth placentas. Autophagosome size was quantified using NIS element software and the diameter was measured at an arbitrary intensity range of 1000-3000, diameter range 0.2-1 µm and circularity range 0.5-1. Analysis showed that post-dated and stillbirth placentas have significantly larger ($p=0.012$ and $p=0.0019$, respectively, Mann Whitney test) autophagosomes than term placentas. Open circles and filled circles represent term caesarean non-labouring placentas (n=11) and term vaginal delivery labouring placentas (n=10), respectively. Open squares and filled squares represent post-dated labouring caesarean placentas (n=8) and post-dated labouring vaginal delivery placentas (n=15), respectively. Filled triangles represents unexplained stillbirth placentas (n=4). Each point in the graph represents the average diameter of LC3B particles in six images taken for each placenta.
Figure 8:
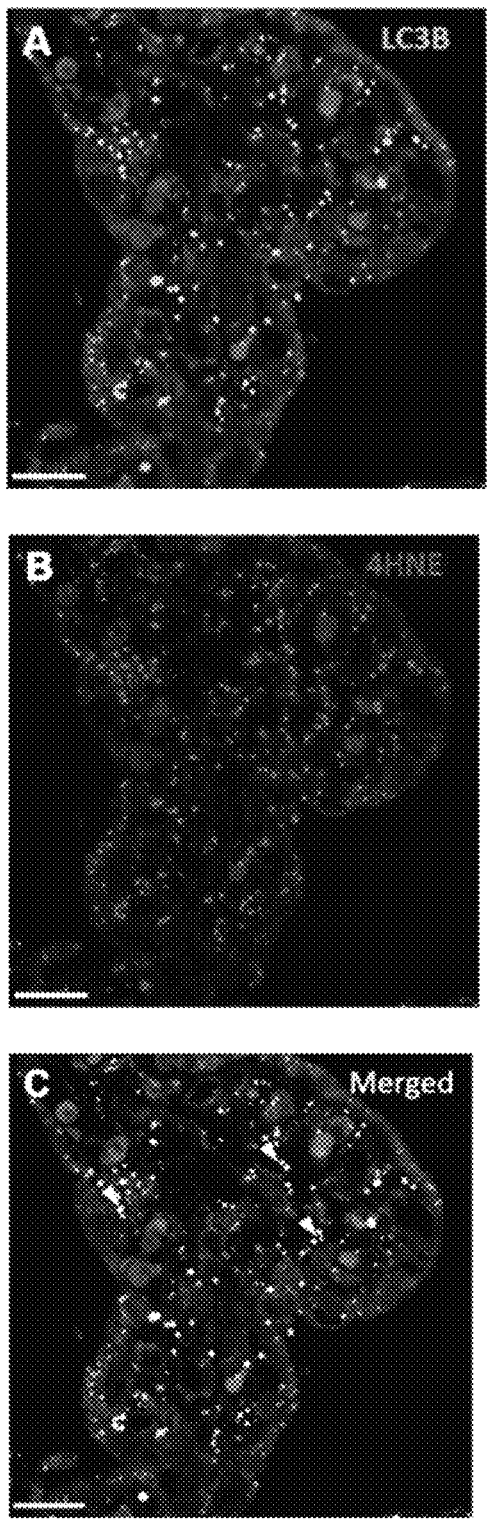
FIG. 8: Oxidised lipids within autophagosomes of post-dated placentas. Representative dual labelled fluorescence immunostaining showed that LC3B, an autophagosome marker is co-localised with 4HNE, a marker of lipid peroxidation. Dots (pointed by arrow heads in C) indicate the co-localization. DAPI staining indicates the nuclei. Original magnifications 100×; scale bar 20 µm.

Example 4—Larger Autophagosomes Containing 4HNE Occur in Post-Dated and Stillbirth Associated Placentas Inhibition of autophagosome function with failure of fusion with lysosomes leads to an increase in autophagosome size. This process leads to inhibition of overall autophagic function that is seen in Alzheimer's disease, Danon's disease, and neurodegeneration. In the present study, the inventors detected autophagosomes using immunohistochemistry with an antibody against LC3B. A significant increase in the size of autophagosomes was observed in both post-dated and stillbirth associated placentas compared to term placentas (FIG. 7). Dual labelled fluorescence immunostaining showed that the larger autophagosomes of post-dated and stillbirth placentas contained 4HNE, a product of lipid peroxidation (FIG. 8).

Autophagy involves fusion of acidic lysosomes with the autophagosome. The present data indicate that stillbirth and post-dated placentas contain larger autophagosomes than term placentas suggesting inhibition of the autophagic process in these placentas. These data further indicate that the autophagosomes are coated with oxidised lipid in the form of 4HNE in the failure of fusion. Such disturbances in the function of autophagosomes may lead to the accumulation of abnormal protein and deterioration in the function of the syncytiotrophoblast.

Example 5—Role of Aldehyde Oxidase 1 (AOX1) in Placental Oxidative Damage

Figure 9:
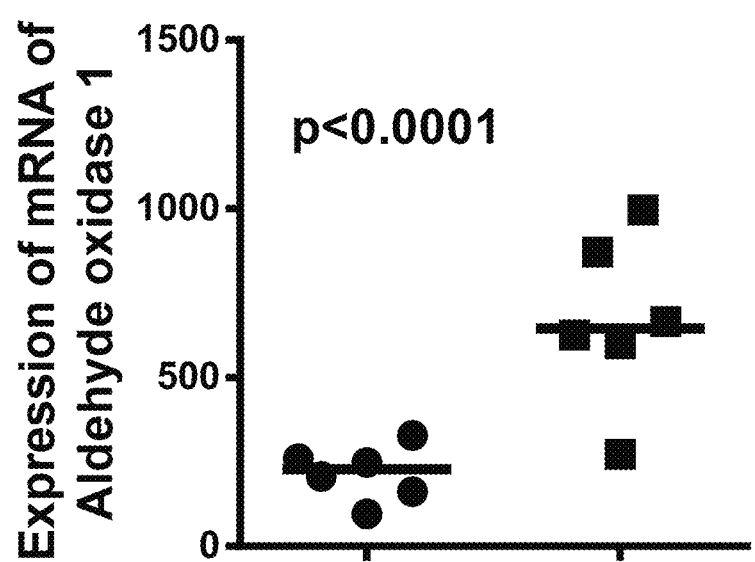
FIG. 9: RNA-sequencing data showed post-dated placentas have significantly higher expression of AOX1 mRNA than term placentas.
Figure 10:
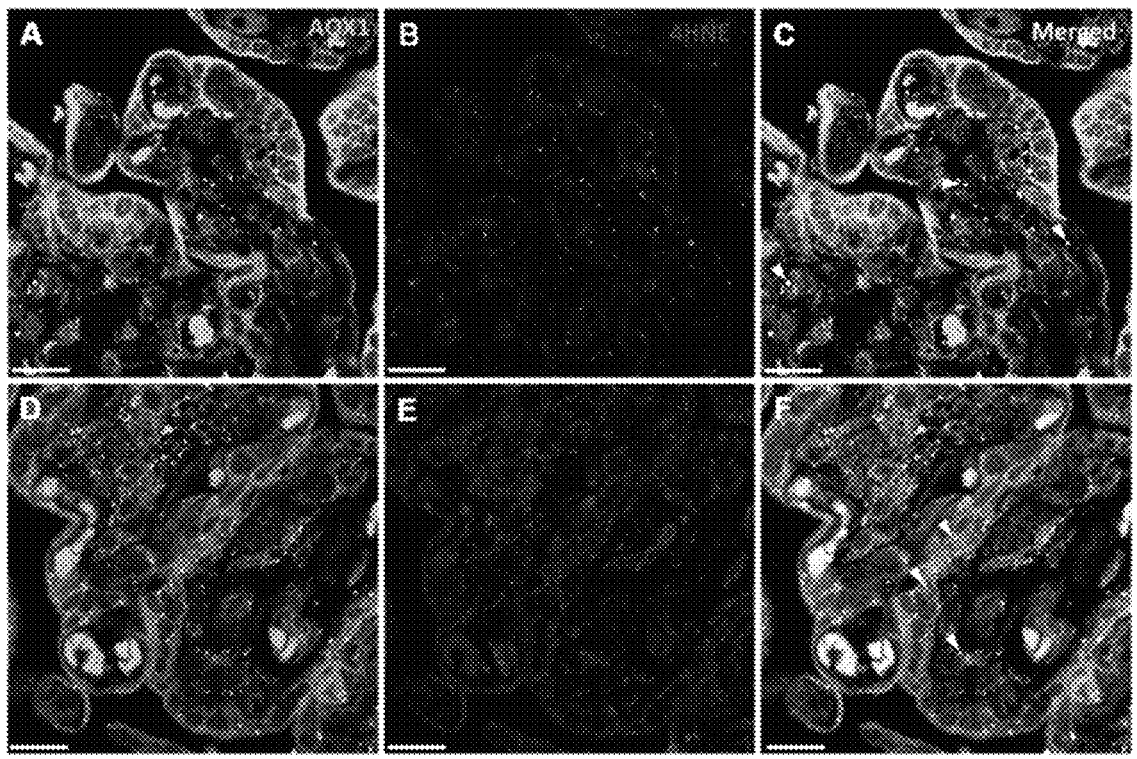
FIG. 10: Role of aldehyde oxidase 1(AOX1) in the production of 4HNE. Representative dual labelled fluorescence immunostaining in post-dated (A-C) and stillbirth (D-F) placentas showed that AOX1 positive particles are co-localized with 4HNE. Dots (pointed by arrow heads in C and F) indicate the degree of co-localization. Nuclei are stained with DAPI. Real-time PCR showed that expression of AOX1 mRNA is increased in post-dated ($p=0.0097$) and stillbirth ($p=0.012$) placentas compared to term placentas (G). Original magnification 100×; scale bar 20 µm.
Figure 10:
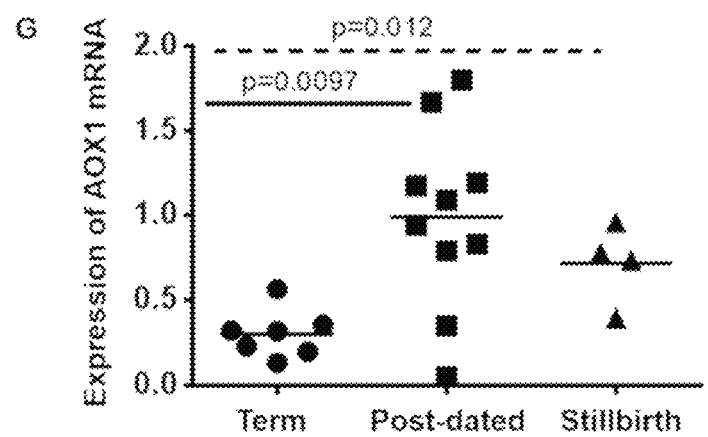
Figure 11:
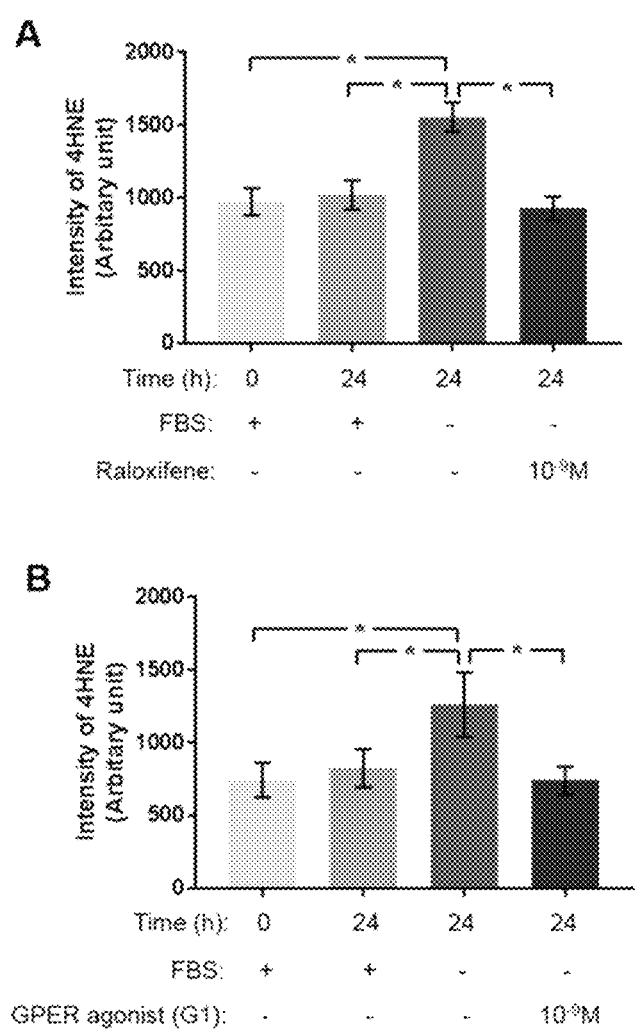
FIG. 11: Pharmacologic inhibition of 4HNE production and expression of GPER1 in placenta. The production of 4HNE (induced by serum starvation) is significantly reduced after treating placental explants with raloxifene, an AOX1 inhibitor (A), and G1, a membrane estrogen receptor GPER1 agonist (B). Data are mean±SEM, *$p<0.05$ (N=6).

Using methods well known to those skilled in the art, the inventors sequenced RNA isolated from six term and six post-dated placentas. Analysis of RNA sequencing data showed that out of the 20111 genes expressed in placentas, aldehyde oxidase 1 (AOX1) was significantly increased in post-dated placentas compared to term placentas (FIG. 9).

AOX1 is a molybdoflavoenzyme which oxidises a range of aldehydes, including 4HNE, into corresponding acids and peroxides. The inventors then tested the hypothesis that AOX1 was involved in the generation of the increased 4HNE observed in post-dated and stillbirth associated placentas. Dual labelled fluorescence IHC showed that AOX1 co-localizes to 4HNE positive particles in post-dated (FIG. 10A-C) and stillbirth placentas (FIG. 10D-F). Additionally real-time qPCR using the Life Technologies TaqMan assay Hs00154079_m1 confirmed that post-dated and stillbirth placentas expressed significantly higher mRNA for AOX1 than term placentas (FIG. 10G). These data support the concept that AOX1 may play a role in the oxidative damage that occurs in the post-dated and stillbirth associated placentas.

Example 6—Pharmacological Inhibition of Production of 4HNE Using Placental Explant Culture The present data provide clear evidence for increased lipid oxidation, disordered lysosome-autophagosome interactions and increased AOX1 expression in the post-dated and stillbirth placental syncytiotrophoblast. To determine if these events were causally linked the inventors developed a placental explant culture system using term placental tissue cultured in serum-free (growth factor deficient) medium. IHC showed that serum deprivation significantly increased production of 4HNE at 24 hr after incubation (FIGS. 11A and B). A significant increase in the size of autophagosomes was also found after 24 hr incubation in serum-free medium (FIGS. 12A and B), suggesting inhibition of autophagy at 24 h by oxidative damage, as observed in the stillbirth and post-dated placentas. mRNA for AOX1 increased at 24 h suggesting involvement of AOX1 in the oxidative damage.

Figure 12:
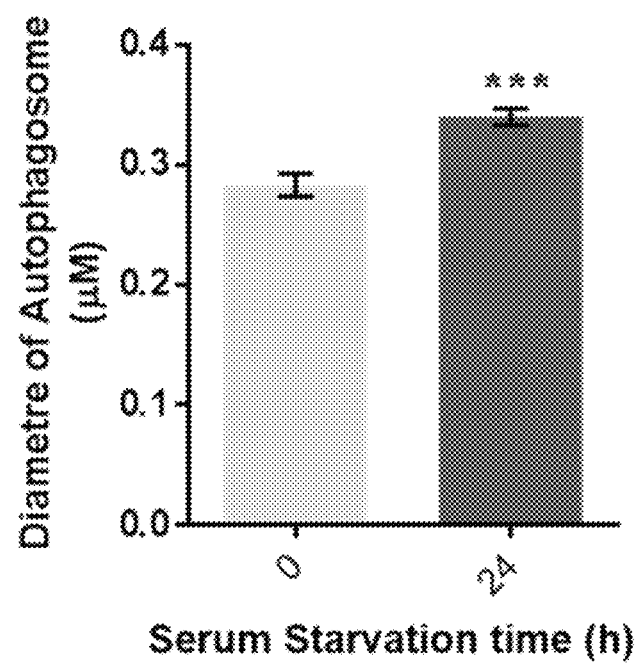
FIG. 12: Changes in autophagosome size in placental explants cultured in serum deprived medium. Immunohistochemical analysis showed that the size of autophagosomes (LC3B positive particles) increased 24 h after serum starvation compared to 0 h. Data presented as mean±SEM, ***p=0.0002 (N=13).

The inventors sought to determine cause and effect relationships between the development of lipid oxidation observed when placental explants were cultured in the absence of serum and AOX1. The GPER agonist G-1 was used to inhibit aldehyde oxidase. The potent AOX1 inhibitor, raloxifene, was also used. G-1 was selected as the inventors had detected GPER expression on the apical surface of syncytiotrophoblast (FIGS. 11C and 11D) and the GPER1 agonist has been shown to inhibit production of 4HNE in the kidney (Lindsey et al., 2011, *Hypertension,* 58: 665-671). Both raloxifene and G1 inhibited the production of 4HNE in the serum starved placental explants after 24 hr of treatment (FIGS. 11A and B), demonstrating these compositions were able to block the oxidative damage to the lipid and also the disturbance in autophagosome size and lysosomal location (FIG. 12).

Example 7—Presence of the Cell Surface Estrogen Receptor GPER1 on the Apical Surface of the Syncytiotrophoblast As G-1 had evident effects in placental explant cultures the inventors undertook characterisation of GPER1 expression in placental tissue. The expression of GPER1 in a section of placenta roll detected by fluorescent immunohistochemistry showed that GPER1 is expressed in placental villi (data not shown), which at higher magnification (100×), was localised to the apical surface of placental villi, whereas term amnion, chorion and decidua showed very little GPER1 expression (data not shown). Fluorescence immunostaining with an antibody against LC3B showed changes in autophagosome size in placental explants after serum starvation (FIG. 12).

Figure 13:
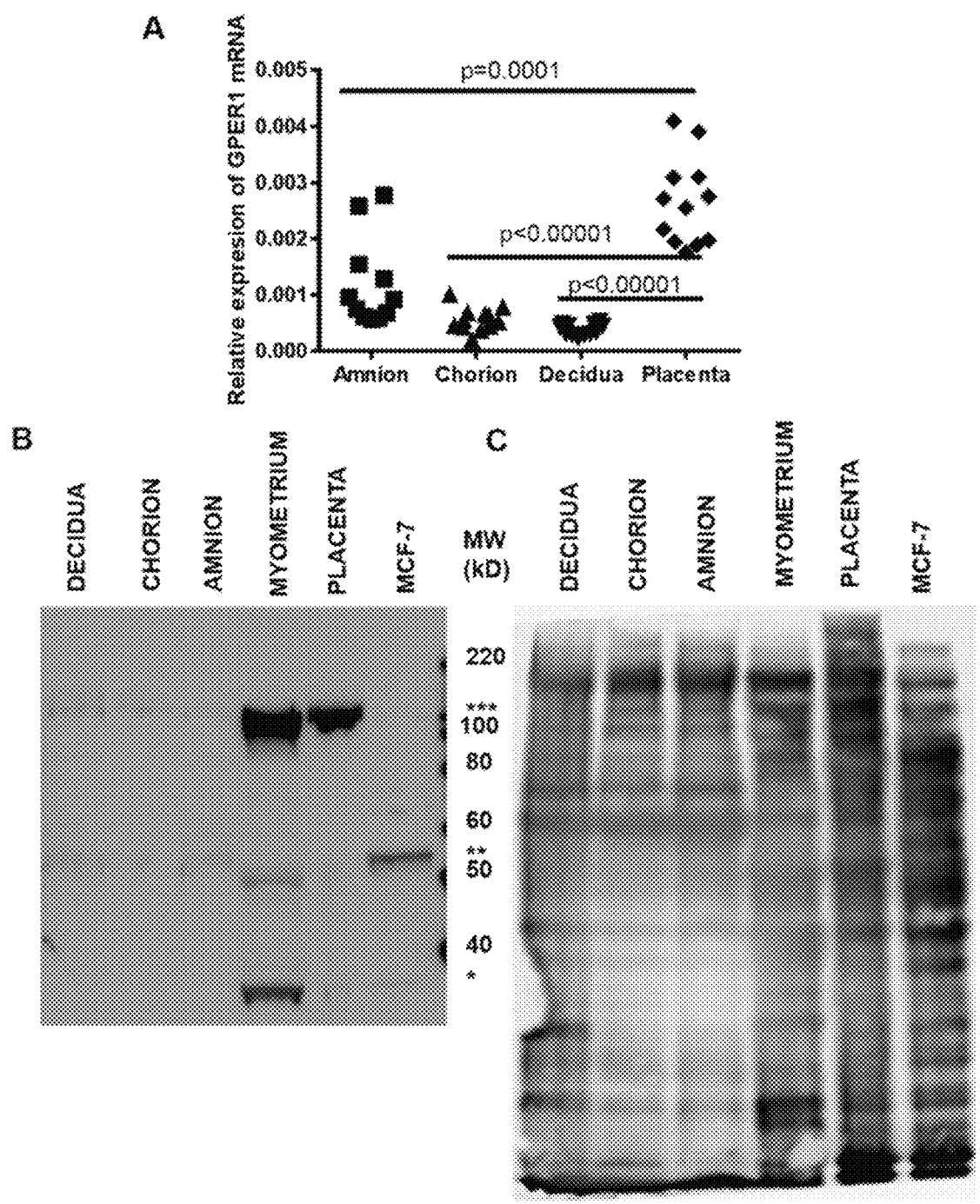
FIG. 13: Detection of GPER1 in different tissues by real-time PCR and western-blotting. The real-time qPCR data showed that the mRNA for GPER1 is expressed in higher amounts in term placenta than in amnion, chorion and decidua (A). The amount of expression of mRNA of GPER1 has the following order in these tissues: decidua<chorion<amnion<placenta (A). The proteins were extracted from the breast cancer cell line MCF-7, term placenta, term myometrium, term amnion, term chorion and term decidua and western-blotting was performed (B). Placenta, myometrium and MCF-7 cell lines expressed higher amounts of GPER1 than amnion, chorion or decidua (B). Western-blotting data showed that all the tissues expressed glycosylated GPER1 (denoted by  or by *) and non-glycosylated nascent GPER1 (denoted by *). The sypro-ruby stain of same PVDF membrane is used as internal loading control (C).

GPER1 primers were sourced from Invitrogen: GPER1 Forward primer 5'-CGTCCTGTGCACCTTCATGT-3' (SEQ ID NO:1) and GPER1 reverse primer 5'-AGCT-CATCCAGGTGAGGAAGAA-3' (SEQ ID NO:2). Real time PCR for GPER1 showed that placental villi have significantly higher expression of GPER1 than amnion, chorion and decidua (FIG. 13A). Western-blot for GPER1 also confirmed higher protein levels of GPER1 in placental villous tissue than amnion, chorion and decidua (FIG. 13B).

The presence of the cell surface estrogen receptor GPER on the syncytiotrophoblast apical membrane is a novel finding and suggests that this receptor may play a role in modulating oxidative damage within the placenta. It has been shown that urine from pregnant women carrying a fetus with post-maturity syndrome have lower estrogen: creatinine ratios than women carrying normal foetuses (Rayburn et al., 1982, *Obstet Gynecol,* 60: 148-153). These data support the possibility that low estrogen concentrations may lead to loss of GPER mediated inhibition of AOX1 and consequently placental oxidative damage and impaired function.

Example 8—Detection of AOX1 mRNA in Maternal Blood

Fetal AOX1 mRNA was detected in maternal blood by methods well known to those skilled in the art. Briefly, maternal blood samples were collected in PAXgene® Blood RNA Tubes. The blood samples were stored at −30° C. until used for RNA isolation. Total RNA in 2.5 ml of total maternal blood samples was isolated using a PAXgene Blood miRNA Kit and fully automated RNA isolation system QIAcube (Qiagen). The quality of RNA from samples was checked by running the RNA samples in a bioanalyser (Agilent Technologies). The value of the ratio of 28 S and 18 S greater than 1 was considered as good quality RNA obtained from total blood. The total RNA was treated with RNAse free DNAse, before it was used for preparation of cDNA. The cDNA was prepared from total RNA using the SuperScript® III First-Strand Synthesis System (Life technologies). The cDNA was used to quantify the mRNA for AOX1 using the Taqman gene expression system and 7500 applied biosystem PCR machine using human 18 S ribosomal RNA as an internal control.

Figure 14:
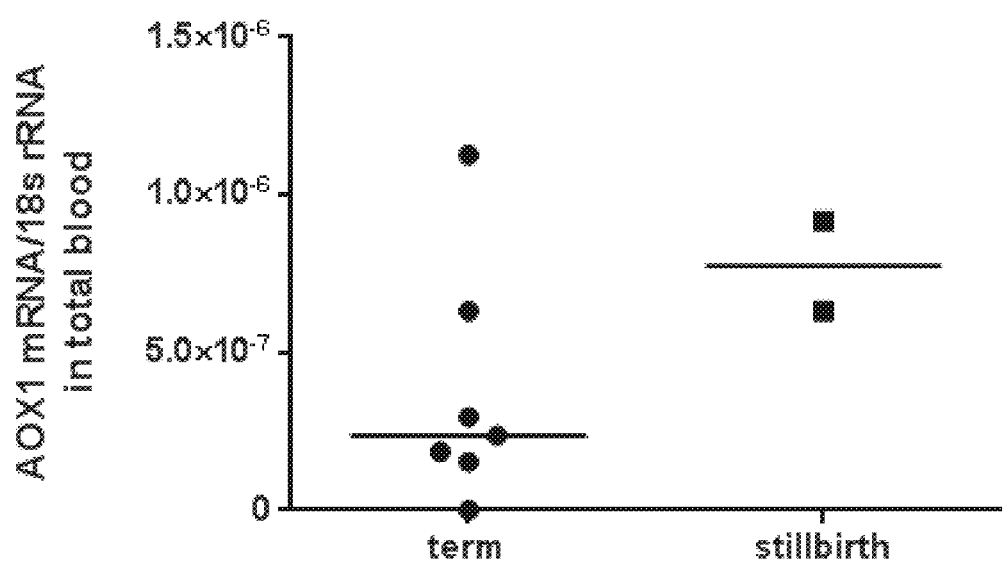
FIG. 14: AOX1 mRNA is increased in total maternal blood in the case of stillbirth as compared to term pregnancies.

The majority of AOX1 mRNA in maternal blood is derived from the placenta and therefore maternal blood AOX1 mRNA may be used as an indicator of placental oxidative stress. The inventors measured maternal blood AOX1 mRNA in seven mothers at term (37-39 completed weeks of gestation) and two women whose pregnancy resulted in a stillbirth blood samples were measured at 31 and 36 weeks gestation. The average amount of AOX1 mRNA was significantly increased in maternal blood in stillbirth as compared to term pregnancies (FIG. 14).

Example 9—Aldehyde Oxidase-Mediated Aging in the Kidney

Figure 15:
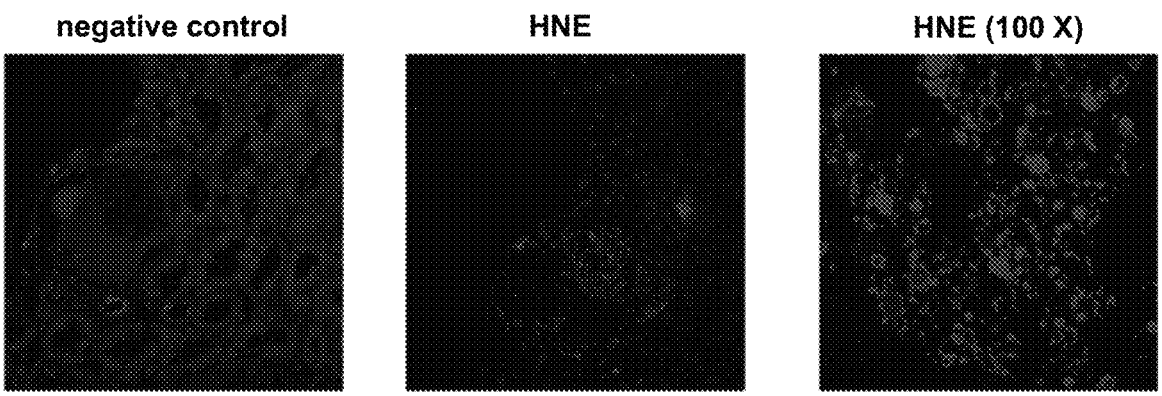
FIG. 15: Immunostaining for 4HNE in kidney tissue from a 66 year old subject (A) and from a 21 year old subject (B). All images are at 20× magnification, unless indicated.
Figure 15:
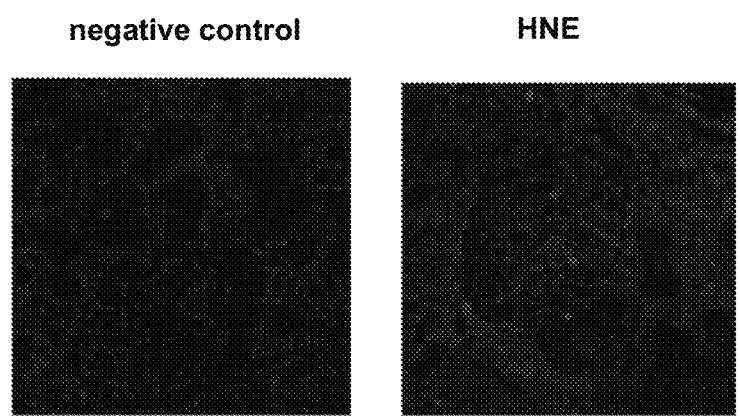

Kidney tissue from a 21 year old subject and a 66 year old subject was stained for 4HNE as a marker of oxidised lipid formed by aldehyde oxidase. The results shown in FIG. 15 demonstrate that aldehyde oxidase causes oxidative damage, a marker of aging, in the kidney. Thus, tissues that express aldehyde oxidase can be aged by oxidative damage.

The invention claimed is:

1. A method of treating a disease or condition associated with ageing or oxidative damage in one or more cells or tissues, the method comprising:

selecting for treatment a subject in which the level of AOX1 expression or activity in a biological sample obtained from the subject, and comprising said cells or tissue, is increased relative to a reference value, wherein said increase in the level of expression or activity, of AOX1 is indicative of aging in said cells or tissue; and administering to said subject in need thereof an inhibitor of aldehyde oxidase 1 (AOX1).

2. The method of claim 1, wherein the subject is pregnant and the tissue is placental tissue.

3. The method of claim 1, wherein the biological sample comprises blood, amniotic fluid, placental tissue or a sample derived therefrom.

4. The method of claim 2, wherein the biological sample is of maternal origin.

5. The method of claim 2, wherein the sample is maternal blood.

6. The method of claim 1, wherein said increased AOX1 expression or activity is determined from free RNA or DNA, fragments of placental cells, exosomes, or microparticles present within the biological sample.

7. The method of claim 1, wherein the level of AOX1 expression or activity is determined by the level of AOX1 mRNA and/or AOX1 protein.

8. The method of claim 7, wherein the level of AOX1 expression or activity is further determined by measuring one or more markers of AOX1 activity, wherein said one or more markers are selected from 8-hydroxy-deoxyguanosine (8OHdG), 8-hydroxy-guanosinne (8HOG), 4-hydroxynonenal (4HNE) and malondialdehyde (MDA).

9. The method of claim 7, wherein the level of AOX1 expression or activity is determined by the level of AOX1 mRNA and/or protein and 4HNE.

10. The method of claim 2, wherein in the pregnant subject an increased level of expression or activity of AOX1, or of the one or more markers thereof, in the biological sample compared to a reference value is indicative of placental aging, pre-eclampsia, intra-uterine growth restriction, risk of post-dated pregnancy risk of stillbirth, a need for intervention to prevent post-dated pregnancy or stillbirth or an appropriate time to deliver a baby.

11. The method of claim 10, wherein the intervention to prevent post-dated pregnancy or stillbirth comprises prophylactic caesarean section, induction of labor and/or administration of a therapy to prevent or delay placenta ageing or prolong viability of the fetus in utero.

12. The method of claim 2, wherein the disease or condition associated with placental aging comprises pre-eclampsia, intra-uterine growth restriction, or stillbirth.

* * * * *